(12) United States Patent
Devore et al.

(10) Patent No.: US 9,271,933 B2
(45) Date of Patent: Mar. 1, 2016

(54) GRAFT COPOLYMER POLYELECTROLYTE COMPLEXES FOR DRUG DELIVERY

(71) Applicant: Rutgers, The State University of New Jersey, New Brunswick, NJ (US)

(72) Inventors: David Devore, Fort Sam Houston, TX (US); Charles Roth, Princeton, NJ (US)

(73) Assignees: RUTGERS, THE STATE UNIVERSITY OF NEW JERSEY, New Brunswick, NJ (US); US ARMY, SECRETARY OF THE ARMY, Fort Detrick, MD (US)

( * ) Notice: Subject to any disclaimer, the term of this patent is extended or adjusted under 35 U.S.C. 154(b) by 0 days.

(21) Appl. No.: 13/828,105

(22) Filed: Mar. 14, 2013

(65) Prior Publication Data

US 2013/0183379 A1 Jul. 18, 2013

Related U.S. Application Data

(63) Continuation-in-part of application No. 12/744,824, filed as application No. PCT/US2008/084995 on Nov. 26, 2008, now Pat. No. 8,962,757.

(60) Provisional application No. 61/619,234, filed on Apr. 2, 2012, provisional application No. 60/990,606, filed on Nov. 27, 2007.

(51) Int. Cl.
| | |
|---|---|
| C12N 15/11 | (2006.01) |
| C08F 293/00 | (2006.01) |
| A61K 9/127 | (2006.01) |
| A61K 47/32 | (2006.01) |
| C12N 15/113 | (2010.01) |

(52) U.S. Cl.
CPC .............. *A61K 9/1272* (2013.01); *A61K 9/1271* (2013.01); *A61K 47/32* (2013.01); *C12N 15/111* (2013.01); *C12N 15/1135* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| 5,776,899 A * | 7/1998 | Matsumoto et al. ........... 514/3.8 |
| 2002/0192275 A1 * | 12/2002 | Zalipsky et al. ............... 424/450 |
| 2003/0096774 A1 * | 5/2003 | Gonda et al. .................... 514/44 |

OTHER PUBLICATIONS

Swati Mishra et al., "Poly(alkylene oxide) opolymers for Nucleic Acid Delivery", Accounts of Chemical Research, vol. 45, No. 7, 2012, 1057-1066.
R. Nagarajan, et al., "Block Copolymer Self-Assembly in Selective Solvents: Theory of Solubilization in Spherical Micelles", Macromolecules, 1989, vol. 22, No. 11, 4312-4325, American Chemical Society.
H. Zhang, et al., "Interaction of a Polycation with Small Oppositely Charged Dendrimers", J. Phys. Chem. B, 1999, 103, 2347-2354, American Chemical Society.
Marcia O. Fenley, et al., "Theoretical Assessment of the Oligolysine Model for Ionic Interactions in Protein-DNA Complexes", The Journal of Physical Chemistry B, 2011, 115, 9864-9872.
Mario Grassi, et al., "Mathematical Modelling and Controlled Drug Delivery: Matrix Systems", Current Drug Delivery, 2005, 2, 97-116.
Paresh Chandra Ray, et al., "Toxicity and Environmental Risks of Nanomaterials: Challenges and Future Needs", J Environ Sci Health C Environ Carcinog Ecotoxicol Ref., Jan. 2009, 27(1), 1-35.
Swati Mishra, et al., "Delivery of siRNA silencing Runx2 using a multifunctional polymer-lipid nanoparticle inhibits osteogenesis in a cell culture model of heterotopic ossification", Integrative Biology, 2012, 4, 1498-1507.
Lavanya Y. Peddada, et al., "Novel graft copolymers enhance in vitro delivery of antisense oligonucleotides in the presence of serum", Journal of Controlled Release, 2009, 140, 134-140.

* cited by examiner

*Primary Examiner* — Richard Schnizer
(74) *Attorney, Agent, or Firm* — Fox Rothschild LLP

(57) ABSTRACT

Graft copolymer polyelectrolyte complexes are disclosed for the efficient delivery of anionic, cationic or polyelectrolyte therapeutic agents into biological cells, and for maintaining the biological activity of these molecules while in serum and other aqueous environments are provided. Such complexes comprise (1) an anionic graft copolymer containing an anionic polymer backbone, with pendent carboxylic acid groups and pendant chains containing amphipathic or hydrophilic polymers covalently bonded to a portion of the pendant carboxylic acid groups, (2) one or more anionic, cationic or polyelectrolyte therapeutic agents, and (3) optionally a liposome optionally containing an additional therapeutic agent. Also disclosed are functional nanoparticles containing the complexes.

14 Claims, 7 Drawing Sheets

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial
<220> FEATURE:
<223> OTHER INFORMATION: Synthetic

<400> SEQUENCE: 1
ttgtggccgt ttacgtcgcc                                                   20

<210> SEQ ID NO 2
<211> LENGTH: 20
<212> TYPE: RNA
<213> ORGANISM: Artificial
<220> FEATURE:
<223> OTHER INFORMATION: Synthetic

<400> SEQUENCE: 2
cagacaagug aagagguuuu                                                   20

<210> SEQ ID NO 3
<211> LENGTH: 20
<212> TYPE: RNA
<213> ORGANISM: Artificial
<220> FEATURE:
<223> OTHER INFORMATION: Synthetic

<400> SEQUENCE: 3
```
aaccucuuca cuugucuguu                                              20

<210> SEQ ID NO 4
<211> LENGTH: 20
<212> TYPE: RNA
<213> ORGANISM: Artificial
<220> FEATURE:
<223> OTHER INFORMATION: Synthetic

<400> SEQUENCE: 4
gcauaaaggg agaagcaguu                                              20

<210> SEQ ID NO 5
<211> LENGTH: 20
<212> TYPE: RNA
<213> ORGANISM: Artificial
<220> FEATURE:
<223> OTHER INFORMATION: Synthetic

<400> SEQUENCE: 5
cugcuucucc cuuuaugcuu                                              20

<210> SEQ ID NO 6
<211> LENGTH: 20
<212> TYPE: RNA
<213> ORGANISM: Artificial
<220> FEATURE:
<223> OTHER INFORMATION: Synthetic

<400> SEQUENCE: 6
auugaagaag aagcacacuu                                              20

<210> SEQ ID NO 7
<211> LENGTH: 20
<212> TYPE: RNA
<213> ORGANISM: Artificial
<220> FEATURE:
<223> OTHER INFORMATION: Synthetic

<400> SEQUENCE: 7
gugugcuucu ucuucaauuu                                              20

<210> SEQ ID NO 8
<211> LENGTH: 20
<212> TYPE: DNA
<213> ORGANISM: Artificial
<220> FEATURE:
<223> OTHER INFORMATION: Synthetic

<400> SEQUENCE: 8
ccctgccctt tgtacacacc                                              20

<210> SEQ ID NO 9
<211> LENGTH: 19
<212> TYPE: DNA
<213> ORGANISM: Artificial
<220> FEATURE:
<223> OTHER INFORMATION: Synthetic

<400> SEQUENCE: 9
cgatccgagg gcctcacta                                               19

<210> SEQ ID NO 10
<211> LENGTH: 19
<212> TYPE: DNA
<213> ORGANISM: Artificial

```
<220> FEATURE:
<223> OTHER INFORMATION: Synthetic

<400> SEQUENCE: 10
ccgcacgaca accgaccat                                                    19

<210> SEQ ID NO 11
<211> LENGTH: 21
<212> TYPE: DNA
<213> ORGANISM: Artificial
<220> FEATURE:
<223> OTHER INFORMATION: Synthetic

<400> SEQUENCE: 11
agccaccaag gctggagtct t                                                 21

<210> SEQ ID NO 12
<211> LENGTH: 18
<212> TYPE: DNA
<213> ORGANISM: Artificial
<220> FEATURE:
<223> OTHER INFORMATION: Synthetic

<400> SEQUENCE: 12
tctcccagcg tgcgccat                                                     18
```

GRAFT COPOLYMER POLYELECTROLYTE COMPLEXES FOR DRUG DELIVERY

CROSS-REFERENCE TO RELATED APPLICATIONS

This application is a Continuation-in-Part under 35 U.S.C. §120 of U.S. patent application Ser. No. 12/744,824, filed on May 26, 2010, which is the U.S. National Stage application under 35 U.S.C. §371 of International Application Serial No. PCT/US2008/84995, filed on Nov. 26, 2008, which claims the benefit of priority under 35 U.S.C. §119(e) of U.S. Provisional Application Ser. No. 60/990,606, filed on Nov. 27, 2007.

This application also claims the benefit of priority under 35 U.S.C §119(e) of U.S. Provisional Application Ser. No. 61/619,234, filed on Apr. 2, 2012. The entire disclosures of all of the above applications are incorporated herein by reference.

STATEMENT REGARDING FEDERALLY SPONSORED RESEARCH OR DEVELOPMENT

This invention was made with government support under Contract No. W81XWH-10-2-0139 and the FY10 Defense Medical Research and Development Program Basic Research Award for Project D61_I_10_J2_235, both of which were awarded by the Department of Defense. The government has certain rights in the invention.

FIELD OF THE INVENTION

This invention relates to materials and methods for intracellular delivery of drug molecules which are otherwise difficult to deliver, including for example, therapeutic cationic peptides, oligonucleotides, other nucleic acids, plasmid DNA encoding genes or ribozymes, peptide nucleic acids, aminoglycoside antibiotics, glycopeptide antibiotics, and lipopeptide antibiotics. Further, co-delivery of other therapeutic agents, including for example, local anesthetics, antitumor agents, imaging agents, fluorescent dyes and quantum dots, can be achieved via incorporation of a liposome.

BACKGROUND OF INVENTION

The ability of exogenously administered nucleotide molecules to mediate gene silencing was discovered nearly 30 years ago. Ever since, this technology has been utilized as a research tool to study gene function, and over time it has been developed for treatment of diseases arising from the abnormal over-expression or over-activity of a particular gene, such as cancer, autoimmune and cardiovascular diseases, wound healing and viral infections. This technology, referred to herein as antisense therapeutics, includes a range of technologies differentiated by the approaches they use to break down the mRNA. Approaches of interest include, for example, RNA interference (RNAi), micro-RNA, and the use of conventional antisense deoxynucleotide technologies.

Further progress in this field requires improvement in the systemic and cellular delivery of these antisense therapeutics to their targets. Some of the barriers at the systemic level include survival against unfavorable interactions with serum proteins present in the bloodstream, avoidance of accumulation in non-target organs such as lung, liver and kidney, and targeting of the diseased or infected cells. Once the antisense therapeutics have overcome these barriers, they must maneuver their way into the target cell and finally to the target mRNA within the cell. Some of the challenges to antisense therapeutic delivery at the cellular level include efficient entry into the cell, escape from degradative lysosomes, and release into the cytoplasm.

While viral vectors are also being used for delivery of such antisense therapeutics and gene delivery, safety concerns persist. Although iterative design of non-viral vectors has endowed them with attributes for overcoming some of the systemic and cellular barriers in the delivery of antisense therapeutics, their delivery efficiencies are generally too low and their cytotoxicities are generally too high. A major barrier to the intracellular delivery of antisense therapeutics is their sequestration in endosomes, which eventually fuse with lysosomes, leading to degradation of their contents.

Accordingly, there is a continuing need in the art for methods and materials that improve intracellular delivery of antisense therapeutics, as well as oligonucleotides and other nucleic acids in general.

Similarly, there is a need in the art for methods and materials to improve intracellular delivery of cationic peptides, peptide nucleic acids, and various antibiotic molecules (aminoglycosides, glycopeptides and lipopeptide antibiotics), with or without co-delivery of other therapeutic agents (drugs).

BRIEF SUMMARY OF THE INVENTION

A first aspect of the invention provides innovative graft polymers designed for the efficient delivery of polynucleotides into biological cells, and for maintaining the biological activity of these molecules while in serum and other aqueous environments. Polynucleotides can include plasmid DNA, synthetic natural or chemically modified oligonucleotides used for gene silencing via antisense or RNA interference mechanisms, ribozymes, aptamers, microRNAs, decoys, etc. Such polymers can comprise an anionic graft polymer comprising an anionic polymer backbone with pendant carboxylic acid groups and pendent chains comprising amphipathic or hydrophilic polymers covalently bonded to a portion of said pendent carboxylic acid groups. The instant polymers preferably have a graft density of between about 0.1 and about 25 mole percent, more preferably between about 0.5 and about 10 mole percent, and most preferably between about 0.5 to about 5 mole percent.

Suitable anionic backbone polymers include, but are not limited to, polyanhydrides, poly(acrylic acids), poly(alkylacrylic acids), carboxymethylcellulose, polyglutamic acids, polyaspartic acids, vinyl copolymers, or combinations thereof. In the preferred embodiments the backbone of the instant polymer comprises poly (propylacrylic acid) or poly (methacrylic acid). Suitable polymers for use as pendent chains, include but are not limited to, polyetheramines, poly (alkylene oxides), or combinations thereof.

In one specific embodiment, such polymers can comprise a backbone comprising a poly(alkylacrylic acid) and one or more polyetheramine pendent chains covalently attached to said polymer backbone via said acrylic acid groups predominantly comprising ethylene oxide repeating units, wherein said polymer has a graft density between about 0.1 and about 25 mole percent.

A second aspect of the invention provides a vector for intracellular delivery of therapeutic polynucleotide molecules, including but not limited to antisense molecules, comprising a graft polymer as described above and at least one cationic agent for delivery of polynucleotides. Suitable cationic agents for delivery of therapeutic polynucleotides molecules include, but are not limited to, surfactants, liposomes, peptides, polymers, micelles, nanoparticles or combinations thereof. Polynucleotides can include plasmid DNA, synthetic natural or chemically modified oligonucleotides used for gene silencing via antisense or RNA interference mechanisms, ribozymes, aptamers, microRNAs, decoys, etc. The delivery vector including an antisense molecule has an electrostatic charge ratio of about −5 to +5 equivalents and a particle size of about 50 nm to about 300 nm.

A third aspect of the invention provides a pharmaceutical composition comprising the delivery vector as described above and a pharmaceutically acceptable carrier. The composition can further comprise a therapeutic polynucleotide such as an antisense DNA or RNA molecule a plasmid DNA or ansiRNA.

A fourth aspect of the invention provides a method of treatment for human or animal diseases including but not limited to cancer and heterotopic ossification. Such method includes silencing the expression of genes, such as oncogenes in cancer cells, by administering to a patient a therapeutically effective amount of the delivery vector as described above further comprising an siRNA targeted to an appropriate gene. In cancer, the gene targeted for silencing might be an anti-apoptotic gene, such as BCL-2. In heterotopic ossification, the target gene might be one such as Runx2 that is in an osteogenic pathway. Without limiting the range that may be required for a particular therapeutic application, the dose of siRNA can be between about 0.1 to about 25 mg/kg, preferably about 0.1 to about 10 mg/kg, more preferably between about 0.1 to about 1 mg/kg.

A further aspect of the invention is directed to a graft copolymer polyelectrolyte complex comprising:
(1) an anionic graft copolymer comprising:
  (i) a backbone comprising a poly(alkyl acrylic acid); and
  (ii) one or more polyetheramine pendent chains covalently attached to said copolymer backbone as amides of the acrylic acid groups, wherein said pendent chains predominantly comprise ethylene oxide repeating units;
  wherein said copolymer has a graft density between about 0.5 and about 25 mole percent;
(2) one or more anionic, cationic or polyelectrolyte therapeutic agents; and
(3) optionally, a liposome which optionally comprises an additional therapeutic agent;
wherein when said therapeutic agent is an antisense molecule, a liposome comprising said additional therapeutic agent is also present.

The pendent chains of the graft copolymer polyelectrolyte complex can further comprise one or more ligands that target a specific cell, tissue or surface. In one embodiment, one or more of said ligands targets a microbial biofilm or a planktonic microbe. In another embodiment, one or more of said ligands comprises a phosphonate molecule that targets bone tissue.

Another aspect of the present invention is directed to a functional nanoparticle comprising the above graft copolymer polyelectrolyte complex, wherein the nanoparticle provides in vitro, ex vivo or in vivo delivery via oral, enteral, parenteral or topical routes of administration of the therapeutic agent.

Yet another aspect of the invention is directed to a method of preparing a graft copolymer-polyelectrolyte complex comprising the steps of:
(1) providing an aqueous mixture of an anionic graft copolymer comprising:
  (i) a backbone comprising a poly(alkyl acrylic acid); and
  (ii) one or more polyetheramine pendent chains covalently attached to said copolymer backbone as amides of the acrylic acid groups, wherein said pendent chains predominantly comprise ethylene oxide repeating units;
  wherein said copolymer has a graft density between about 0.1 and about 25 mole percent;
(2) adding one or more polyelectrolytes to form a polyelectrolyte-copolymer mixture;
(3) optionally adding an aqueous mixture containing a liposome which optionally comprises an additional therapeutic agent, to form a liposome-containing polyelectrolyte-copolymer mixture; and
(4) allowing said polyelectrolyte-copolymer mixture or said liposome-containing polyelectrolyte-copolymer mixture to self-assemble in the aqueous medium to form said complex, which further forms nanoparticles.

Still another aspect of the invention is directed to a method of treating a patient in need thereof with a polyelectrolyte therapeutic agent comprising the steps of:
(1) formulating the complex or the nanoparticle of any of the above with one or more pharmaceutically acceptable carriers to provide a pharmaceutical composition; and
(2) administering said pharmaceutical composition to said patient via oral, parenteral, enteral or topical routes in an amount effective to treat said patient.

DETAILED DESCRIPTION OF PREFERRED EMBODIMENTS

Figure 1:
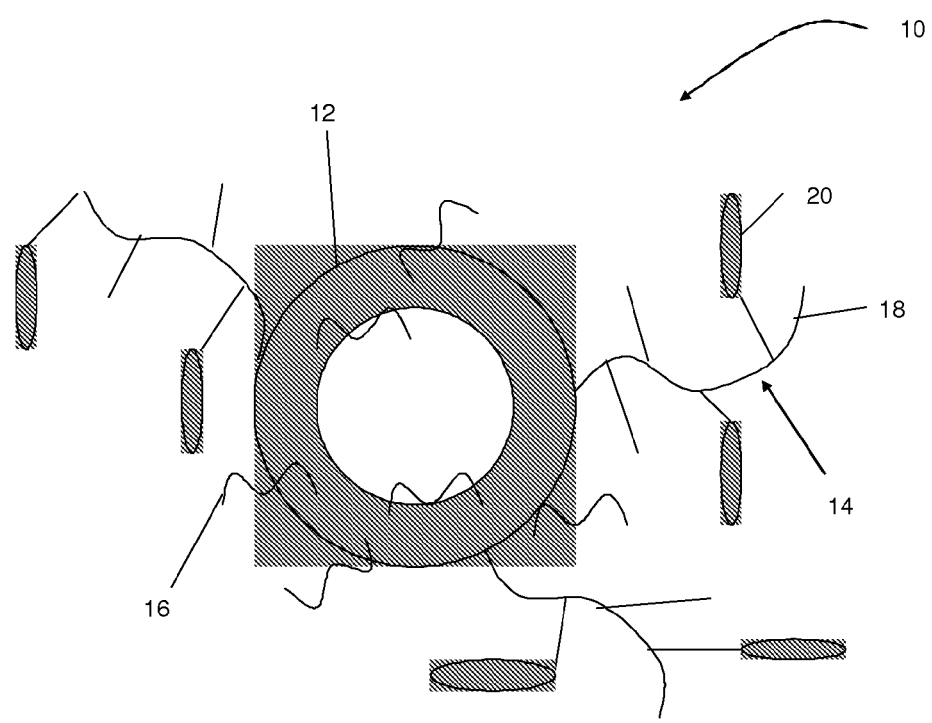
FIG. 1 presents a diagram of a delivery complex of the invention.
Figure 2:
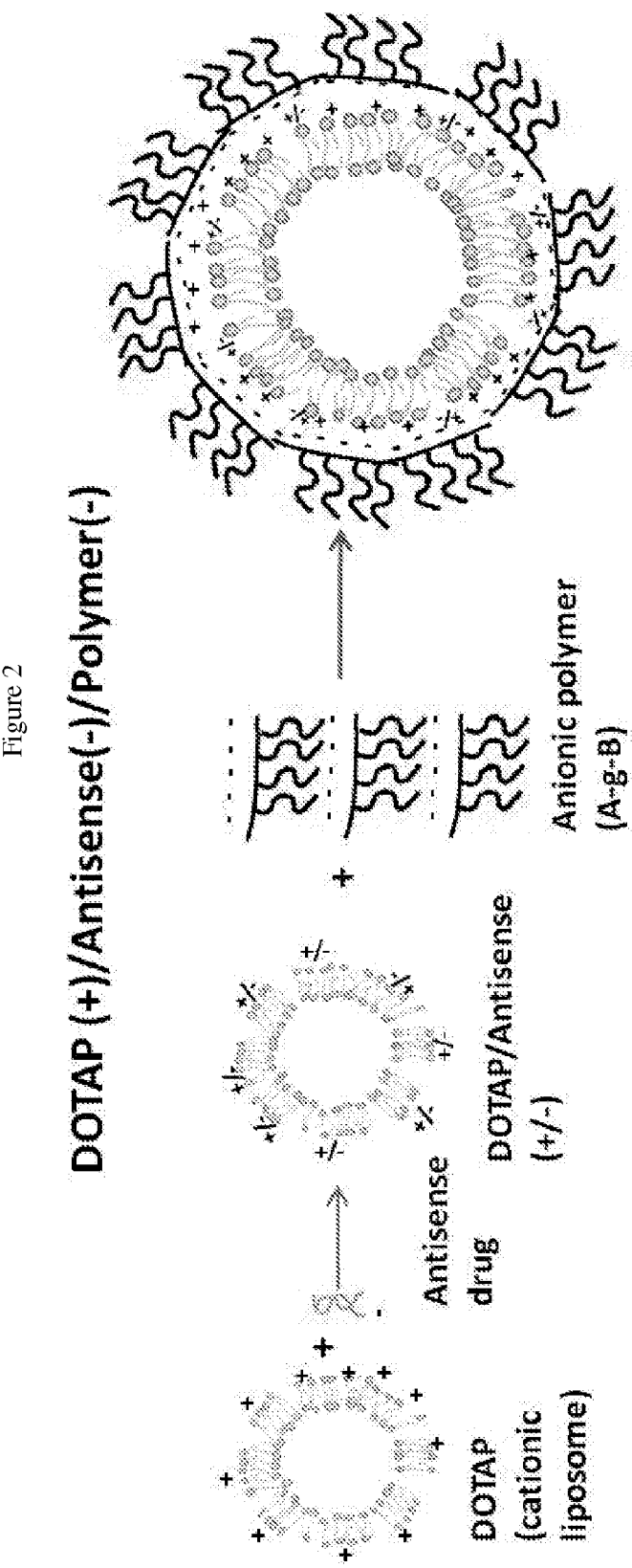
FIG. 2 presents a diagram of the morphological structure of a typical liposome-polymer carrier system of the invention (antisense oligonucleotide; AON).
Figure 3:
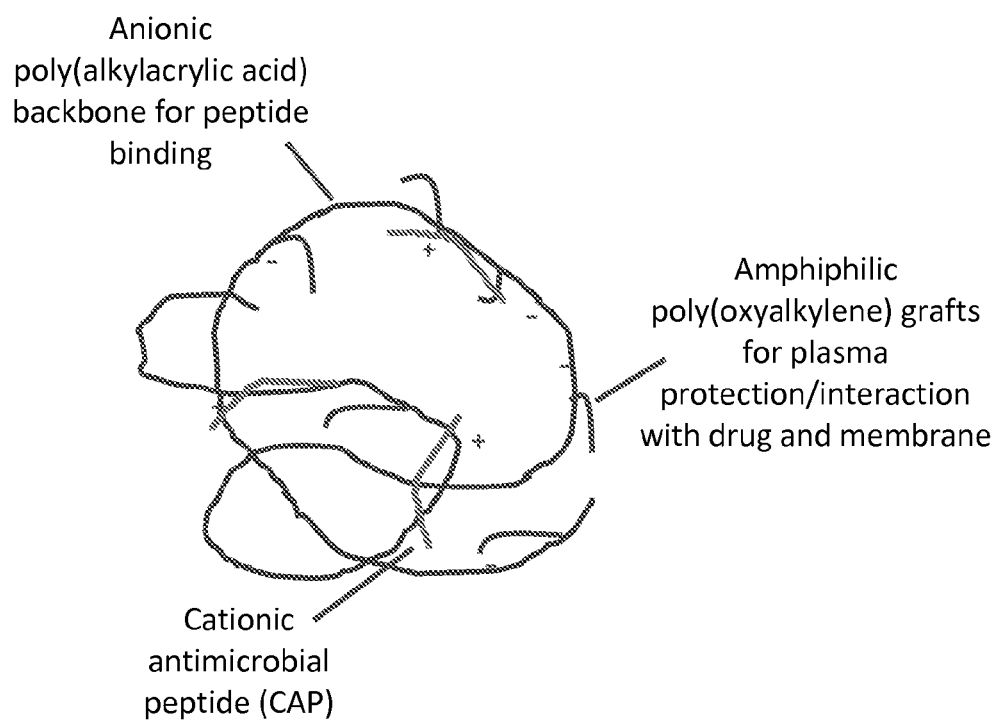
FIG. 3 presents a diagram of the various components of a typical graft copolymer polyelectrolyte complex (cationic antimicrobial peptide).

One aspect of the invention provides innovative graft polymers designed for the efficient delivery of antisense molecules into biological cells and for maintaining the biological activity of the antisense molecules while in serum and other aqueous environments. Such graft polymers can comprise an anionic graft polymer comprising an anionic polymer backbone, referenced herein as backbone polymer with pendent carboxylic acid groups, and pendent chains comprising amphipathic or hydrophilic polymers, referenced herein as pendent chain polymers covalently bonded to a portion of said pendent carboxylic acid groups.

Suitable backbone polymers include, but are not limited to, polyanhydrides, poly(acrylic acids), poly(alkylacrylic acids), anionic polysaccharides such as carboxymethylcellulose, anionic polypeptides such as polyglutamic acid and polyaspartic acid, and vinyl copolymers comprised of monomers such as alkyl acrylates, alkyl methacrylates, acrylamidomethylpropane sulfonic acid (AMPS), vinyl alcohol, and vinyl acetate, or combinations thereof. Preferably, the backbone polymer comprises poly(alkyl acrylic acid), most preferably poly(methacrylic acid) or poly(propylacrylic acid).

The term "hydrophilic polymer," as used herein, means any macromolecule (molecular weight of 200 daltons and greater) which exhibits an affinity for or attraction to water molecules and which comprises multiple instances of an identical subunit ("monomer") connected to each other in chained and/or branched structures. The hydrophilic polymer component can be a synthetic or naturally occurring hydrophilic polymer.

Naturally occurring hydrophilic polymers include, but are not limited to: polypeptides and proteins such as collagen and derivatives thereof, fibronectin, albumins, globulins, fibrinogen, and fibrin, with collagen particularly preferred; carboxylated polysaccharides such as polymannuronic acid and polygalacturonic acid; aminated polysaccharides, particularly the glycosaminoglycans, e.g., hyaluronic acid, chitin, chondroitin sulfate A, B, or C, keratin sulfate, keratosulfate and heparin; and activated polysaccharides such as dextran and starch derivatives.

Useful synthetic hydrophilic polymers include, but are not limited to: poly(alkylene oxides), particularly poly(ethylene glycol) and poly(ethylene oxide)-poly(propylene oxide) copolymers, including block and random copolymers; polyols such as glycerol, polyglycerol (in particular, highly branched polyglycerol), propylene glycol and trimethylene glycol substituted with one or more poly(alkylene oxides), e.g., mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; acrylic acid polymers and analogs and copolymers thereof, such as poly(acrylic acid) per se, poly(methacrylic acid), poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), and poly(N-isopropylacrylamide); poly(olefinic alcohol)s such as poly(vinyl alcohol); poly(N-vinyl lactams) such as poly(vinyl pyrrolidone), poly(N-vinyl caprolactam), and copolymers thereof; polyoxazolines, including poly(methyloxazoline) and poly(ethyloxazoline; and polyvinylamines.

Preferred embodiments utilize poly(ethylene glycol) (PEG), also known as poly(ethylene oxide) (PEO), having a molecular weight of from about 1 kDA to about 10 kDa, more preferably from about 2 kDa to about 5 kDa, and a general formula (II).

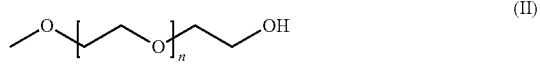

(II)

The term "amphipathic polymer," as used herein, refers to any macromolecule (molecular weight of 200 daltons and greater) which have both polar substructures and non-polar substructures. The polar substructures evidence an affinity for or attraction to other polar molecular structures such as water (hydrophilic), while the nonpolar substructures exhibit an affinity or attraction for nonpolar molecules such as lipids, oils, greases, fats, etc. (lipophilic). Suitable amphipathic polymers include, but are not limited to, polyether and polyetherester copolymers such as poly(ethylene glycol) and poly(butylene terephthalate) copolymers, poly(ethylene oxide) and poly(propylene oxide) copolymers, poly(ethylene oxide) and poly(propylene oxide) block copolymers.

The amphipathic polymers also include polyetheramines such as those known commercially as JEFFAMINE®. These polyetheramines contain primary amino groups attached to the end of a polyether backbone which is typically based on propylene oxide (PO), ethylene oxide (EO), or a mixture thereof. The JEFFAMINE® family includes monamines, diamines, triamines and secondary amines. JEFFAMINE® is available from Huntsman Corporation, The Woodlands, Tex. By way of non-limiting example, certain embodiments can employ a JEFFAMINE® Monoamine having a molecular weigh of about 2 kDA, PO/EO ratio of 10/31 and a general formula (III):

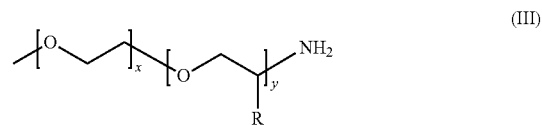

(III)

wherein R is H for EO or $CH_3$ for PO.

The instant graft polymers can be synthesized by reacting carboxylic acid groups of the backbone polymer with the end group of the pendent chain polymers. In general, a backbone polymer can be added to a polar aprotic solvent, such as dimethylsulfoxide (DMSO), along with a catalyst, such as 4-(dimethylamino)pyridinium p-toluenesolfonate (DPTs) or 1-hydroxybenzotriazole (HOBt) and a pendent chain polymer. The amount of graft chain polymer can be in a slight molar excess required to achieve the desired amount of the graft chain polymer attached to the backbone. A carboxyl activating agent, such as 1-(3-dimethylaminopropyl)-3-ethyl-carbodiimide (EDCI), can be added to the mixture after stirring the mixture for a short period of time. The reaction is then allowed to proceed and is driven to completion with subsequent additions of the carboxyl activating agent. The mixture can then be dialyzed against deionized water before converting the polymer into a form suitable for storage, such as by lyophilizing the dialyzed solution.

The term "graft density," as used herein, refers to the average percent on a molar basis of pendent carboxyl groups on the backbone of the graft polymer which react with the end group of the pendent chain polymers. The graft density for instant graft polymers is preferably between about 0.1 and about 25 mole percent, more preferably between about 0.5 and 10 mole percent, and most preferably between about 0.5 and 5 mole percent. The amount of the graft chain polymer can be calculated based on molar or weight percent. In some embodiments, the instant graft polymer comprises greater than 50 percent by weight of the pendent chain polymer. The extent of grafting, molecular weight, molecular dimensions and electrostatic properties of the copolymers and complexes are characterized by nuclear magnetic resonance (NMR) and Fourier transform infra-red (FT-IR) spectrometry, gel permeation chromatography (GPC), light scattering and zeta potentials.

By way of non-limiting example, a graft polymer can comprise a backbone comprising a poly(alkyl acrylic acid) and one or more polyetheramine pendant chains covalently attached to said polymer backbone via said acrylic acid groups. The polyetheramine can predominantly comprise ethylene oxide repeating units. Preferably, such a polymer has a graft density between about 0.1 and about 25 mole percent.

Another aspect of the invention provides vectors for delivery of antisense molecules into cells, tissues and organs in vitro, ex vivo or in vivo. The term "vector," as used herein, refers to a carrier into which aa therapeutic or diagnostic agent can be inserted or to which a therapeutic or diagnostic molecule can be attached for introduction into a cell, tissue or organ. Instant vectors can comprise the graft polymers described above bound to at least one cationic agent. The term "cationic agent," as used herein, refers to a substance suitable for delivery of polynucleotide molecules and having a positive net charge at physiological pH. Suitable cationic agents for delivery of polynucleotides such as antisense molecules include, but are not limited to cationic lipids, surfactants, liposomes, micelles, peptides, polymers, nanoparticles or combinations thereof.

Cationic liposomes or micelles can be prepared using mixtures including one or more lipids containing a cationic side group in sufficient quantity such that the liposomes or micelles formed from the mixture possess a net positive charge which will ionically bind negatively charged compounds. Suitable lipids, as identified by the Dermatologic and Ophthalmic Drug Advisory Committee (DODAC) of the US FDA, include, but are not limited to N-[1-(2,3-dioleyloxy) propyl]-N,N,N-trimethylammonium chloride (DOTMA), dimethyldioctadecylammonium bromide (DDAB), 1,2-dioleoyl-3-trimethylammonium-propane chloride (DOTAP), 3β-[N—(N',N'-dimethylaminoethane)-carbamoyl]cholesterol hydrochloride (DC-Chol) and 1,2-dimyristyloxypropyl-3-dimethyl-hydroxyethyl ammonium bromide (DMRIE). Additionally, a number of commercial preparations of cationic liposomes are available which include, for example, LIPOFECTIN® comprising DOTMA and dioleoyl phosphatidylethanolamine (DOPE), and LIPOFECTAMINE® comprising 2,3-dioleyloxy-N-[2(sperminecarboxamido) ethyl]-N,N-dimethyl-1-propanaminium trifluoroacetate (DOSPA) and DOPE.

Cationic surfactants include, but are not limited to, quaternary ammonium salts, for example, didodecyldimethylammonium bromide (DDDAB), alkyltrimethylammonium bromides such as hexadecyltrimethylammonium bromide (HDTAB), dodecyl-trimethylammonium bromide (DTMAB), myristyl trimethylammonium bromide (MTMAB), palmityl trimethylammonium bromide, N-alkylpyridinium salts, or tertiary amines, for example, cholesteryl-3β-N-(dimethyl-aminoethyl)-carbamate or mixtures thereof. Cationic peptides can be selected from naturally occurring or recombinant or synthetic peptides produced by known means. Examples of suitable cationic peptides include, but are not limited to magainins, polymyxins, colicins, alamethicin, pexiganan or MSI-78, and other MSI peptides such as MSI-843 and MSI-594, polyphemusin, human antimicrobial peptide, LL-37, KSL, KSL-W, defensins and protegrins. Finally, suitable examples of cationic polymers include, but are not limited to, acidic gelatin, polygalactosamine, polyamino acids such as polylysine, polyhistidine and polyornithine, polyquaternary compounds such as poly(allylamine) and poly(diallyldimethyl ammonium chloride) (DADMAC), polyethylenimine (PEI), polybrene, prolamine, polyimine, diethylaminoethyldextran (DEAE), DEAE-imine, DEAE-methacrylate, DEAE-acrylamide, DEAE-dextran, DEAE-cellulose, poly-p-aminostyrene, polyoxethane, copoly- methacrylates, polyamidoamines, cationic starches, polyvinylpyridine, and polythiodiethylaminomethyl-ethylene.

Alternatively or additionally, the vectors can comprise the graft polymers in combination with organic or inorganic nanoparticles. It is desirable to use nanoparticles that are biocompatible and hydrophilic, and range in size between about 10 nm and 300 nm, and more preferably between about 50 nm and 150 nm Biodegradable or resorbable nanoparticles are preferred.

The instant delivery vectors form ternary delivery complexes with polynucleotides such as antisense molecules and plasmid DNA. The term "antisense molecule," as used herein, refers to ribonucleic acid (RNA) sequences, deoxyribonucleic acid (DNA) sequences and their derivatives encoding said ribonucleic acid sequences, which cause RNA interference and/or, via other biological mechanisms, decrease or silence expression of the target gene. The antisense molecules are sufficiently complementary to the sequence of DNA or mRNA encoding a target gene so as to have the proper antisense or interfering property. Suitable antisense molecules include, without limitations, antisense oligodeoxynucleotides, short hairpin RNAs (shRNAs), short interfering RNAs (siRNAs), microRNAs (miRNAs), and DNA-RNA hybrids. Oligonucleotide synthesis is well known in the art. The term "target gene," as used herein, refers to a gene whose expression is to be selectively inhibited or silenced through RNA interference or related mechanism because its expression or activity is associated with a particular disease. For example, cancer can arise from abnormal expression or activity of a gene associated with the inhibition or prevention of apoptosis, such as Bcl-2, Bcl-XL, Bcl-w, Mcl-1, and/or A1. Accordingly, in one embodiment, the antisense molecule is a siRNA targeted to an anti-apoptotic gene.

These complexes can be self-assembled from their individual components through electrostatic interactions. Generally, aqueous solutions of the cationic agent for delivery of antisense molecules and the antisense molecule can be incubated at room temperature for about 30 minutes, before adding the instant graft polymer to produce the desired charge ratio of the complex. The term "charge ratio," as used herein, refers to a ratio of the moles of amine groups of the cationic agent to the number of moles of phosphate groups of the antisense molecule, carboxylic groups of the graft polymer, or a sum thereof. Preferably, the absolute value of the charge ratio of the cationic to anionic components of the complexes disclosed herein is between about 0.1 and about 10, more preferably between about 0.5 and about 2, and most preferably about 1.

In one embodiment of the present invention, the nanoparticle (liposome) self-assembles without the anionic polymer (in the presence or absence of polynucleotide such as antisense oligonucleotide or siRNA). To this established nanostructure, polynucleotides are first incorporated physically, and then graft copolymer is adsorbed. The purpose of the anionic polymer is not just to stabilize the nanostructure, but primarily is to endow the nanostructure with the necessary attributes to overcome nucleic acid delivery barriers.

One embodiment is directed to a stable and biocompatible delivery vector comprising an anionic graft polymer comprising an anionic polymer backbone with pendent carboxylic acid groups and pendent chains of amphipathic or hydrophilic moieties covalently bonded to a portion of the pendent carboxylic acid groups, wherein (a) the anionic graft polymer is physically bound to a complex comprising at least one cationic agent physically bound to at least one anionic antisense molecule, (b) the absolute value of the positive-to-negative (+/−) charge ratio of the delivery vector ranges from about 0.25 to about 4.7 between the anionic graft polymer and the complex of the cationic agent and the antisense molecule, (c) the molecular weights of the covalently bonded amphipathic or hydrophilic moieties are between about 200 Daltons and about 5,000 Daltons, and (d) the anionic polymer has a graft density between about 5 and about 25 mole percent.

The graft density affects the anionic charge density of the anionic graft polymer, as each covalently bound grafted carboxylic acid group reduces by one the number of anionic carboxylic acid charges in the polymer backbone. The resultant charge density of the graft copolymer is important to forming the complex with the cationic agent and antisense molecule through electrostatic interactions. The solution stability of the resultant delivery vector is dependent upon its net electrostatic charge (the greater the net charge, the more soluble the delivery vector will be in physiological solutions, all other parameters being equal).

The graft density of the anionic graft copolymer also controls the biological response to the delivery vector in a manner which is entirely surprising and unanticipated by any other reported study. Without wishing to be bound by any theory, it is believed that the graft density controls the interaction with the amphiphilic bilayers of eukaryotic cell membranes and thereby controls the efficacy of intracellular delivery of the antisense molecules. Thus, the degree of membrane penetration, as measured by a calcein dye leakage assay, decreases with increasing graft density, due to steric interaction between the copolymer and the membrane (see, for example, Mishra et al., *Acc. Chem. Res.*, 45:1057-1066 (2012). There are profound and surprising effects of pH on the interaction of the anionic graft copolymers with cell membranes that are dependent on the graft chemistry and the graft density, and, in the absence of any grafting the anionic polymer produces adverse cytotoxic membrane interactions including significant red cell lysis that is entirely inhibited by the graft copolymers.

An important aspect of the invention is exploiting such dependencies for effective intracellular delivery (endosomal escape) of polynucleotides without associated cytotoxicity. There is also a profound and surprising effect of graft density on the efficacy of delivery of the polynucleotide molecules. The grafted chains provide protection of the polynucleotide molecule within the delivery vector from hydrolytic biodegradation by providing a corona around the outer surface of the delivery vector that inhibits its binding to serum protein enzymes. The chains must be covalently grafted to the anionic polymer in order for this effect to be sustained under physiological conditions, as ungrafted chains rapidly solubilize and dissociate from the delivery vector.

FIG. 1 presents an example of the instant delivery complex (10) comprising a cationic agent (12), graft polymers (14), and polynucleotides (16). Each graft polymer (14) comprises a backbone polymer (18) and pendant chain polymer (20). Despite the overall charge neutrality of the complex, the instant graft polymers do not induce aggregate formations. Thus, the instant delivery complexes form stable particles in various buffer solutions with particle sizes ranging from about 25 to about 300 nm. Furthermore, addition of instant graft polymers preferably does not alter the binding ability of the cationic agents for the polynucleotide molecules.

Yet another aspect provides pharmaceutical compositions comprising delivery vectors bound to polynucleotide molecules, as described above, and one or more pharmaceutically acceptable carriers. The term "pharmaceutically acceptable carrier," as used herein, refers to a non-toxic, inert solid, semi-solid or liquid filler, diluent, encapsulating material or formulation auxiliary of any type. Many different pharmaceutically acceptable carriers are well known in the pharmaceutical arts. Some examples of pharmaceutically acceptable carriers include, but are not limited to, sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations.

In addition, the instant compositions can include excipients such as solvents, binders, fillers, disintegrants, lubricants, suspending agents, surfactants, viscosity increasing agents, buffering agents, antimicrobial agents, adjuvants such as alum, among others. Acceptable excipients and methods for making various compositions are well known in the pharmaceutical arts.

The compositions can be prepared in a solid or liquid form for oral, parenteral, enteral or topical administration. Suitable examples of solid formulations include, but are not limited to, tablets, pills, lozenges, dragees, powders, granules, capsules, etc. Solid formulations can include an optional pharmaceutically acceptable carrier. Suitable examples of liquid formulations include, but are not limited to, solutions, dispersions, emulsions, gels, hydrogels, pastes, creams, aerosols, sprays, syrups, slurries, suspensions, and so forth. Liquid formulations can be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations can also be prepared by the reconstitution of a solid, for example, from a sachet.

Instant compositions can be delivered by rapid release systems, modified release systems, or systems which can provide a part of the dose by modified release and the rest by rapid release. Various approaches are known and used in the art to prepare immediate release systems or modified release systems. Many of these methods are well known in the pharmaceutical arts. Examples of immediate release systems include, but are not limited to, conventional tablets or capsules, or solutions. Examples of modified release systems include, but are not limited to, coated pellets, tablets or capsules; multiple unit or multiparticulate systems in the form of microparticles or nanoparticles, microspheres or pellets comprising the active agent; formulations comprising dispersions or solid solutions of active compound in a matrix, which can be in the form of a wax, gum, fat, or polymer; devices, in which drug is attached to an ion exchange resin, which provides for gradual release of drug by way of influence of other ions present in the gastrointestinal tract, for example, the acid environment of the stomach; devices, such as osmotic pumps, in which release rate of drug is controlled by way of its chemical potential; systems in which drug is released by diffusion through membranes, including multilayer systems, nebulizers, and so forth.

In preferred embodiments, the instant compositions are prepared for parenteral administration. Parenteral administration is generally characterized by a subcutaneous, intramuscular, inhalation or intravenous injection. Compositions of instants delivery complexes for parenteral administration can be prepared as liquid solutions or suspensions, solid forms suitable for solution or suspension in liquid prior to injection, or as emulsions.

Another aspect of the invention is directed to methods for treating a subject who is affected by a disease or at risk of developing a disease that can be treated by inhibiting or silencing a target gene, i.e, a gene associated with the disease. Such methods comprise administering to a patient a therapeutically effective amount of a composition comprising one or more delivery vectors, as described above, bound to one or more polynucleotide molecules designed to interfere with the target gene. Diseases that can be treated by the instant methods include, but are not limited to, cancer, hetertopic ossification, neurological diseases, genetic disorders and chronic wounds such as diabetic ulcers. Without limiting the range that may be required for a particular therapeutic application, the dose of siRNA can be between about 0.1 to about 25 mg/kg, preferably about 0.1 to about 10 mg/kg, more preferably between about 0.1 to about 1 mg/kg.

The terms "silence," "decrease the expression of" and "inhibit the expression of", in as far as they refer to a target gene, herein refer to the at least partial suppression of the expression of the target gene, as manifested by a reduction of the amount of mRNA transcribed from the target gene and/or a reduction in the amount of protein encoded by the target gene, which can be isolated from a first cell or group of cells in which the target gene is transcribed and which has or have been treated such that the expression of the target gene is inhibited, as compared to a second cell or group of cells substantially identical to the first cell or group of cells but which has or have not been so treated (control cells). Alternatively, the degree of silencing, decreasing or inhibiting can be given in terms of a reduction of a parameter that is functionally linked to target gene transcription, e.g. the extent of mineralization by osteogenic cells, or the number of cells displaying a certain phenotype, e.g. apoptosis.

The term "therapeutically effective amount" means a quantity of the active agent which, when administered to a patient, is sufficient to result in an improvement in the patient's condition. The improvement does not mean a cure and may include only a marginal change in patient's condition. It also includes an amount of the active agent that prevents the condition or stops or delays its progression. The term "treating" or "treatment" refers to executing a protocol, which can include administering one or more drugs to a patient (human or otherwise), in an effort to alleviate signs or symptoms of the disease. Alleviation can occur prior to signs or symptoms of disease appearing, as well as after their appearance. Thus, "treating" or "treatment" includes "preventing" or "prevention" of the disease. In addition, "treating" or "treatment" does not require complete alleviation of signs or symptoms, does not require a cure, and specifically includes protocols which have only a marginal effect on the patient.

In one specific embodiment, methods are provided for silencing oncogenic expression in cancer cells. This can be achieved by administering to a patient who is affected or at risk of developing cancer a therapeutically effective amount of a composition comprising one or more polynucleotide molecules designed to silence oncogenic expression in cancer cells in conjunction with instant delivery vectors. The antisense molecules can target a single gene or multiple genes associated with cancer.

In some embodiments, the antisense can comprise a siRNA targeted to an anti-apoptotic gene, such as Bcl-2, Bcl-XL, Bcl-w, Mcl-1, and/or A1. Additional examples of genes which can be targeted include, without limitation, an oncogene; genes of proteins that are involved in metastasizing and/or invasive processes; genes of proteases as well as of molecules that regulate apoptosis and the cell cycle; genes that express the EGF receptor; genes that express the bone morphogenetic proteins (BMPs) or their downstream effectors; and the multi-drug resistance 1 gene, MDR1 gene.

A further aspect of the invention is directed to a graft copolymer polyelectrolyte complex comprising:
  (1) an anionic graft copolymer comprising:
    (i) a backbone comprising a poly(alkyl acrylic acid); and
    (ii) one or more polyetheramine pendent chains covalently attached to said copolymer backbone as amides of the acrylic acid groups, wherein said pendent chains predominantly comprise ethylene oxide repeating units;
  wherein said copolymer has a graft density between about 0.1 and about 25 mole percent;
  (2) one or more anionic, cationic or polyelectrolyte therapeutic agents; and
  (3) optionally, an additional therapeutic agent which is optionally a liposome comprising an additional therapeutic agent;
wherein when said therapeutic agent comprises an anionic polynucleotide molecule, a liposome comprising said additional therapeutic agent is also present. Preferably the copolymer backbone comprises poly(propylacrylic acid) or poly (methacrylic acid). Preferably the copolymer has a graft density between about 0.1 and about 25 mole percent. Many drug molecules can potentially be co-delivered with the complex, including anticancer drugs, antimicrobials, anti-inflammatory agents, analgesics, imaging agents such as fluorescent dyes and quantum dots.

The pendent chains of the graft copolymer polyelectrolyte complex can further comprise one or more ligands that target a specific cell, tissue or surface such as solid tumors or microbial biofilms. Without limitation, ligands may target in animals or humans tumor cells, tumor associated fibroblasts or macrophages, stem or progenitor cells, bone cells, muscle cells, liver cells, and immune cells. Alternatively, ligands may target features from microbial populations. In one preferred embodiment the ligands comprise phosphonates and target bone tissue.

A "polyelectrolyte" is a macromolecular species that upon being placed in water, or any other ionizing solvent, dissociates into a highly charged polymeric molecule. Such dissociation is typically accompanied by smaller oppositely charged counter ions that tend to neutralize the charge on the repeating units of the macromolecule, thereby preserving electroneutrality.

The anionic, cationic or polyelectrolyte therapeutic agent can be selected from the group consisting of cationic peptides, peptide nucleic acids, aminoglycoside antibiotics, glycopeptide antibiotics, lipopeptide antibiotics, aminoamide local anesthetics, aminoester local anesthetics, oligonucleotides, nucleic acids, plasmid DNA-encoding genes, and ribozymes. Preferably, the aminoglycoside antiobiotic is selected from the group consisting of neomycin, gentamicin and tobramycin. Preferably, the glycopeptide antibiotic is selected from the group consisting of vancomycin and telavancin. Preferably, the lipopeptide antibiotic is daptomicin. Preferably, the aminoamide local anesthetics and aminoester local anesthetics are selected from the group consisting of mepivacaine, lidocaine, bupivacaine, benzocaine and procaine.

Preferably, the additional therapeutic agent is selected from the group consisting of small molecule therapeutic agents, anti-tumor agents, imaging agents, fluorescent dyes and quantum dots. Preferably, the small molecule therapeutic agents are selected from the group consisting of anticancer agents, wound healing agents, tissue regeneration agents, other antibiotic agents, and pain control agents.

In one embodiment of the invention, therapeutic agent comprises a cationic peptide. Particularly preferred cationic peptides are selected from the group consisting of KSL-W, colistin and polymyxin B. These polycationic therapeutic agents are stabilized toward biological degradation in vivo by incorporation into stable complexes with the inventive anionic graft copolymers. These complexes can comprise binary complexes of the anionic graft copolymers with cationic peptides, or they can comprise ternary complexes of anionic graft copolymers, liposomes (cationic, anionic or neutral) and cationic peptides. The binary or ternary complexes of the anionic graft copolymers, cationic peptides and optionally liposomes are prepared by self-assembly in aqueous media. The cationic peptides are selected for therapeutic activity such as the treatment of infections in burns and wounds or for cancer chemotherapy. The anionic graft copolymers are specifically comprised of poly(alkyl acrylate) "backbones" to which are covalently attached pendent "chains" of polyetheramines and poly(alkylene oxides). Optionally, the pendent chains contain end-group ligands that are designed to target specific biological cells, tissues or surfaces, including microbial biofilms and planktonic microbes. Examples of the poly(alkyl acrylate) include poly (acrylic acid), poly(methacrylic acid), poly(ethylacrylic acid) and poly(propylacrylic acid). Examples of the pendent polyetheramines include JEFFAMINE® products from Huntsman Corporation, which are typically monoamines at the end of a polymer of ethylene oxide (EO), propylene oxide (PO) or a mixture of EO and PO. Examples of the pendent poly (alkylene oxides) are polymers of EO, PO, butylene oxide (BO) and mixtures of these. The liposomes are comprised of lipids such as cholesterol and other neutral, anionic or cationic lipids, e.g., 1,2-dipalmitoyl-sn-glycero-3-phosphocholine (DPPC) and 1,2-dipalmitoyl-sn-glycero-3-phospho-(1'-myoinositol) (DPPI). The anionic surface charge on the liposomes is useful in electrostatically binding the cationic peptides. The binary and ternary complexes can be formulated to provide a wide range of cationic peptide dosages useful for achieving therapeutic activity.

Peptide-based therapeutics promise to revolutionize treatment for multi-drug resistant microbial infections, cancer and other diseases, but peptide susceptibility to enzymatic hydrolysis in vivo has limited their clinical use. For example, a number of cationic peptides such as polymyxin B and KSL-W are known to have antimicrobial properties, but degrade within a few hours in vivo. For clinical translation, an effective delivery vehicle for these peptides is required that is structurally and synthetically simple and forms uniform, soluble complexes with a variety of peptide drugs to protect them from degradation and enhance their biological activity. Graft copolymers with synthetically tunable chemical properties have the potential to fulfill these requirements. The present invention provides for anionic graft copolymers with optional liposome components that complex the cationic peptides and thereby inhibit biodegradation of the cationic peptides. Although not wishing to be bound by any theory, it is believed that binding to the anionic graft copolymers protects the cationic peptides from the activity of the reticuloendothelial system at least in part through "stealth" steric hindrance properties imparted by the pendent polyetheramine chains. This solves the problem of in vivo delivery of therapeutic cationic peptides, which are otherwise too rapidly biodegraded to allow for effective drug activity.

The binary and ternary complexes of the invention further provide controlled release of the therapeutic agents, for example a cationic peptide, by providing for controlled release rates of the peptides such that sufficient dosage levels can be achieved and maintained over time as required for therapeutic activity. The binary and ternary complexes are able to penetrate biofilms to deliver the therapeutic agents, for example an antimicrobial peptide, and thereby eradicate the biofilms. The binary and ternary complexes also enter eukaryotic cells to deliver the therapeutic agents, e.g., to treat intracellular bacterial infections, or cancer.

Another aspect of the present invention is directed to a functional nanoparticle comprising the above graft copolymer polyelectrolyte complex, where the nanoparticle provides in vivo delivery of the anionic, cationic or polyelectrolyte therapeutic agent. The side chains of the graft copolymer have been found to promote self-assembly into nanoparticles in aqueous solutions, and to influence the critical aggregation concentrations.

Nanoparticle surface charges and size distributions for polyelectrolyte complexes of the graft copolymers with cationic peptides polymyxin B and KSL-W, as well as the cationic antibiotic gentamicin, are found to be dependent upon the component cationic:anionic charge ratios. The effects of graft density and charge ratio on the degradation rates of the peptide-graft copolymer complexes can be assessed using HPLC analysis. We have now discovered that copolymer complexation retains drug activity and in some cases may enhance it.

Yet another aspect of the invention is directed to a method of preparing a graft copolymer-polyelectrolyte complex comprising the steps of:
  (1) providing an aqueous mixture of an anionic graft copolymer comprising:
    (i) a backbone comprising a poly(alkyl acrylic acid); and
    (ii) one or more polyetheramine pendant chains covalently attached to said copolymer backbone as amides of the acrylic acid groups, wherein said pendant chains predominantly comprise ethylene oxide repeating units;
  wherein said copolymer has a graft density between about 0.1 and about 25 mole percent;
  (2) adding one or more polyelectrolytes to form a polyelectrolyte-copolymer mixture;
  (3) optionally adding an aqueous mixture containing an additional therapeutic agent which is optionally a liposome which comprises an additional therapeutic agent, to form a liposome-containing polyelectrolyte-copolymer mixture; and
  (4) allowing said polyelectrolyte-copolymer mixture or said liposome-containing polyelectrolyte-copolymer mixture to self-assemble in the aqueous medium to form said complex, which further forms nanoparticles.

Still another aspect of the invention is directed to a method of treating a patient in need thereof with a polyelectrolyte therapeutic agent comprising the steps of:
  (1) formulating the complex or the nanoparticle of any of the above with one or more pharmaceutically acceptable carriers to provide a pharmaceutical composition; and
  (2) administering said pharmaceutical composition to said patient in an amount effective to treat said patient.

Preferably, the therapeutic agent is selected from the group consisting of antibacterial agents, anticancer agents, wound treatment agents and tissue regeneration agents. The administration can be via oral, parenteral, enteral or topical delivery. Preferably, the pharmaceutical composition is selected from the group consisting of injectable aqueous solutions, injectable aqueous dispersions, aerosols, coatings, hydrogels, topical creams, topical ointments, and wound treatment compositions.

In another aspect of the present invention, it is also possible to co-deliver multiple agents at the same time using this technology. For example, the co-delivery of antisense oligonucleotides along with the chemotherapeutic drug, doxorubicin, has been demonstrated, with indications that internalization of both species occurs in breast cancer cells. Thus, any of the above graft copolymer-drug complexes can be delivered by any of the various above routes, alone or in mixtures, so that multiple targets (for example, pain, infection, and wound healing) can be simultaneously addressed. Also, theranostic approaches, where an imaging agent and therapeutic compound are co-delivered to assure that the drug is reaching its target and to monitor the response to treatment, are possible. Many applications exist in the treatment of cancer, cardiovascular and other diseases, where imaging of the disease can help treatment in multiple ways.

EXAMPLES

Example 1

Graft Copolymers with Poly(Propylacrylic Acid) Backbone for Antisense Delivery

Materials. Poly(α-propylacrylic acid) and poly(acrylic acid) were purchased from Polymer Source. Poly(ethylene glycol)monomethyl ether MW=2000 was purchased from Aldrich. Poly(ethylene glycol)monomethyl ether MW=5000 was purchased from Fluka. 1-(3-dimethylaminopropyl)-3-ethyl-carbodiimide (EDCI) was purchased from Kawaguchi Chemical Industry Co., Ltd. Tokyo, JAPAN. 4-(dimethylamino)pyridinium 4-toluenesulfonate (DPTs) was synthesized following literature procedures. 1-hydroxybenzotriazole (HOBt) was purchased from Aldrich. All reagents were used as received.

1.1 Synthesis of poly(acrylic acid)-graft-5% poly(ethylene glycol)monomethyl ether copolymer.

One possible reaction for synthesizing this polymer is presented in the scheme below.

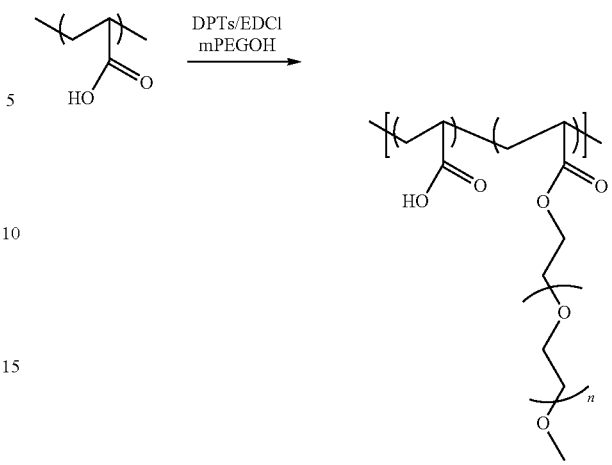

Poly(acrylic acid) (PAA) (0.1 g, 1.38 mmol repeat units), poly(ethylene glycol)monomethyl ether (mPEG2000) (MW=2000, 140 mg, 70 µmol), 4-(dimethyl-amino)pyridinium 4-toluenesulfonate (DPTs) (30 mg, 102 µmol), and 5 mL dimethylsulfoxide were charged into a 10 mL round bottom flask with a magnetic stir bar. The mixture was stirred for 30 min until the reagents dissolved. Next, 1-(3-dimethylaminopropyl)-3-ethyl-carbodiimide (EDCI) (133 mg, 694 µmol) was charged into the reaction. The reaction was stirred for 3 weeks, 2 days at room temperature. EDCI (100 mg, 522 µmol) was added on days 4, 9, and 11. The reaction was transferred to a Slide-A-Lyzer cassette with 10,000 molecular weight cut-off (MWCO) and dialyzed against deionized water for 3 weeks, exchanging water 2-3 times per day except on weekends (6 days) to remove urea side product, DPTs catalyst, and any unreacted mPEG2000. The dialyzed solution was transferred to a 15 mL centrifuge tube, frozen on dry ice, and lyophilized for 1 week. (Yield: 33%) $^1$H NMR (DMSO-d$_6$) δ 1.07 (s), 2.28 (br, CH), 3.23 (s, OCH$_3$), 3.32 (t), 3.53 (s, —OCH$_2$CH$_2$O—), 3.67 (t), 3.99 (s), 4.18 (s, C(O)OCH$_2$CH$_2$OPEG), 4.65 (s), 4.68 (br).

1.2 Synthesis of poly(α-propylacrylic acid)-graft-1% poly(ethylene glycol)monomethyl ether copolymer.

One possible reaction for synthesizing this polymer is presented the scheme below.

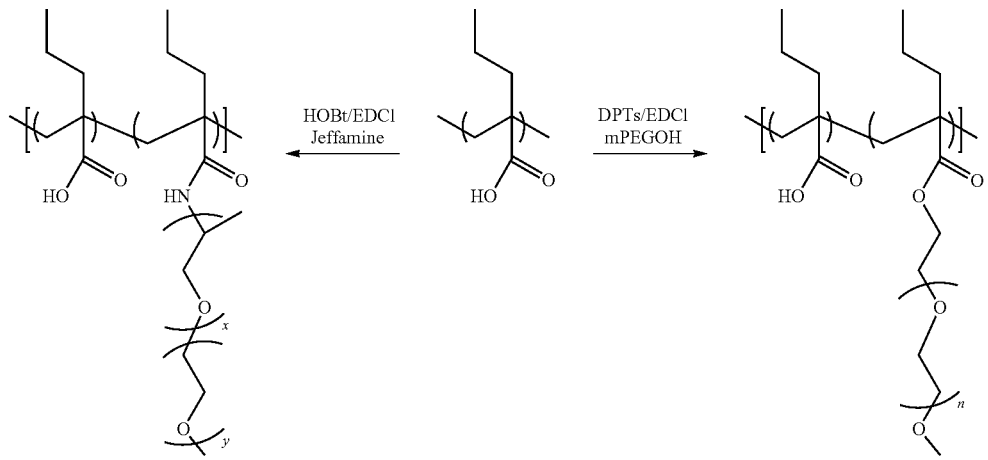

Poly(α-propylacrylic acid) (PPAA) (0.2 g, 174 mmol repeat units), poly(ethylene glycol)monomethyl ether (mPEG2000) (MW=2000, 36 mg, 18 µmol), 4-(dimethylamino)pyridinium 4-toluenesulfonate (DPTs) (11 mg, 37 µmol), and 5 mL dimethylsulfoxide were charged into a 10 mL round bottom flask with a magnetic stir bar. The mixture was stirred for 30 min until the reagents dissolved. Next, 1-(3-dimethylaminopropyl)-3-ethyl-carbodiimide (EDCI) (41 mg, 214 µmol) was charged into the reaction. The reaction was stirred for 3 weeks, 2 days at room temperature. EDCI (100 mg, 522 µmol) was added on days 4, 9, and 11. The reaction was transferred to a Slide-A-Lyzer cassette with 10,000 MWCO and dialyzed against deionized water for 3 weeks, exchanging water 2-3 times per day except on weekends (6 days) to remove urea side product, DPTs catalyst, and any unreacted mPEG2000. The dialyzed solution was transferred to a 15 mL centrifuge tube, frozen on dry ice, and lyophilized for 1 week. (Yield: 22%) $^1$H NMR (DMSO-$d_6$) δ 0.80 (s, $CH_3$), 0.95-2.0 (m, br, $CH_2$(PPAA), 2.10 (br), 2.17 (br), 2.29 (br), 2.35, 2.41, 2.64, 2.77, 2.9-3.3 (br), 3.2 ($OCH_3$), 3.29 (t), 3.47 (s, —$OCH_2CH_2O$—), 3.65 (t), 4.10 (br, C(O) $OCH_2CH_2OPEG$), 4.6-4.8 (br), 4.9-5.2 (br), 7.05 (br), 8.45 (br).

1.3 Synthesis of poly(α-propylacrylic acid)-graft-1% JEFFAMINE® monomethyl ether copolymer.

One possible reaction scheme for synthesizing this polymer is presented above. Poly(α-propylacrylic acid) (PPAA) (0.2 g, 174 mmol repeat units), JEFFAMINE® monomethyl ether (mJEFFAMINE®2000) (MW=2000, 35 mg, 18 µmol), 1-hydroxybenzotriazole (HOBt) (7.5 mg, 56 µmol), and 5 mL dimethylsulfoxide were charged into a 10 mL round bottom flask with a magnetic stir bar. The mixture was stirred for 30 min until the reagents dissolved. Next, 1-(3-dimethylaminopropyl)-3-ethyl-carbodiimide (EDCI) (33 mg, 172 µmol) was charged into the reaction. The reaction was stirred for 3 weeks, 2 days at room temperature. EDCI (100 mg, 522 µmol) was added on days 4, 9, 11. The reaction was transferred to a Slide-A-Lyzer cassette with 10,000 MWCO and dialyzed against deionized water for 3 weeks, exchanging water 2-3 times per day except on weekends (6 days) to remove urea side product and any unreacted mJEFFAMINE®. The dialysis medium used on days 11 and 12 was 0.5 M $NaHCO_3$, in order to remove HOBt, the catalyst. The dialyzed solution was transferred to a 15 mL centrifuge tube, frozen on dry ice, and lyophilized for 1 week. (Yield: 9%) $^1$H NMR (DMSO-$d_6$) δ 0.82 (s, $CH_3$), 1.0-2.0 (br, $CH_2$), 2.10, 2.17, 2.2-3.0 (br), 2.9-3.0 (br), 3.2 ($OCH_3$), 3.24-3.42 (m, $CH+CH_2$ (PPO), 3.47 (s, —$OCH_2CH_2O$—), 3.50, 3.51, 3.52, 3.65 (t), 4.6-4.8 (br), 5.0-5.3 (br), 5.50 (s), 7.08 (d), 7.45-7.60 (br), 7.66 (C(O)NH).

1.4 Synthesis of Additional Copolymers.

Slight modifications the synthetic procedures recited in Examples above can be used to generate an array of copolymers as described herein and summarized in Table 1 below.

Graft copolymers can be prepared with mPEG 5000 in similar fashion as those prepared with mPEG 2000 per the protocol recited above (i.e., in Synthesis of PPAA-1 mol % mPEG 2000) with the following modifications. Preparation of copolymers with mPEG 5000 required the addition of methylene chloride to become a homogeneous solution. At the end of the reaction, prior to dialysis, the reaction was concentrated by rotary evaporation to remove methylene chloride. The reaction was stirred at room temperature for 2 weeks, 6 days and dialyzed with three media exchanges per day for 10 days except on the weekend (2 days). Samples were lyophilized for 4 days.

TABLE 1

Summary of Reaction Specifics for Graft Copolymer Synthesis.

| PPAA (g) | Graft | Graft (g) | DPTs (g) | HOBt (g) | EDCI (initial) (g) | EDCI (aliquot size) (g) | Solvent (mL) |
|---|---|---|---|---|---|---|---|
| 0.199 | mPEG2000 | 0.0358 | 0.0109 | — | 0.041 | 0.1 | 5 |
| 0.1983 | mPEG2000 | 0.168 | 0.0388 | — | 0.167 | 0.17 | 5 |
| 0.2009 | mPEG2000 | 0.3513 | 0.081 | — | 0.33 | 0.33 | 5 |
| 0.2018 | mPEG2000 | 0.88 | 0.202 | — | 0.83 | 0.82 | 5 |
| 0.2018 | mPEG5000 | 0.0865 | 0.0116 | — | 0.1 | 0.1 | 5 + 1.5 |
| 0.2015 | mPEG5000 | 0.4346 | 0.0421 | — | 0.16 | 0.2 | 5 + 2.5 |
| 0.203 | mPEG5000 | 0.869 | 0.0819 | — | 0.33 | 0.4 | 8 + 5 |
| 0.203 | mPEG5000 | 2.181 | 0.215 | — | 0.83 | 0.4 | 8 + 8 |
| 0.2006 | mJeff2000 | 0.035 | — | 0.0075 | 0.033 | 0.1 | 5 |
| 0.1901 | mJeff2000 | 0.17 | — | 0.013 | 0.167 | 0.17 | 5 |
| 0.2001 | mJeff2000 | 0.35 | — | 0.03 | 0.33 | 0.33 | 5 |
| 0.1994 | mJeff2000 | 0.88 | — | 0.0758 | 0.83 | 0.82 | 5 |

Graft copolymers were synthesized with 5 mol % mPEG2000 or mJEFFAMINE®2000 in similar fashion as those prepared with 1 mol % of the pendent chains per the respective protocols recited above (i.e., in Synthesis of PPAA-1 mol % mPEG 2000 and Synthesis of PPAA-1 mol % mJEFFAMINE® 2000) with the following modifications. Preparation of copolymers with 5 mol % mPEG2000 or mJEFFAMINE® 2000 required stiffing at room temperature for 11 days, with only one portion of EDCI (170 mg) being added after 4 days, and also a final concentration of the preparation in a vacuum oven at 40° C. overnight. The products were redissolved in water for dialysis.

1.5 Polymer Characterization.

NMR spectroscopy was performed on a Varian 400 MHz spectrometer. For $^1$H NMR spectra, d1=1s with 32-88 scans was used and ca. 10 mg of sample was dissolved in 0.75-1 mL DMSO-$d_6$. Graft copolymers with mPEG5000 were prepared in $CDCl_3$. Molecular weights of the polymers were determined by GPC using Viscotek GPC max VE2001 GPC solvent/sample module, two ViscoGEL™ Columns, and a Viscotek TDA 303 triple detector array. The triple detection consists of a right angle light scattering detector, a differential viscometer, and a differential refractometer that was purchased from Viscotek Corporation (Houston, Tex., USA). The mobile phase used was DMF with 0.1% TFA at 1.0 mL $min^{-1}$ Polymer sample solutions (5 mg $mL^{-1}$, accuracy to 0.001 mg) were filtered through 0.45 µm nylon syringe filters prior to injection. The temperature for the SEC column set and the detector chamber was set at 35° C. Data acquisition and calculation were performed using Viscotek's OmniSEC software, version 4.1. Conventional GPC was used to determine the molecular weights and polydispersity of each of the polymers and to monitor the reaction on a Waters 510 HPLC equipped with a Waters 410 Differential Refractometer, a 5 μm PL gel precolumn, and two PL gel columns (pore size $10^3$-$10^5$ Angstroms), which was calibrated with polystyrene standards using DMF containing 0.1% trifluoroacetic acid at 0.8 mL min$^{-1}$ as the mobile phase.

Percent grafting was calculated by integration of methylene protons of the ester group (C(O)OCH$_2$CH$_2$PEGOCH$_3$) relative to the methyl protons of PPAA. The Mark-Houwink parameters were obtained from the Viscotek GPC based on a fit of the data of log intrinsic viscosity vs. log MW. Characterization data are presented in Table 2 below.

TABLE 2

Summary of graft polymer characterization data.

| Target Polymer | Target Graft Density (mol %) | Experimental Graft Density (1H NMR) (mol %) | Mark-Houwink log K | Mark-Houwink a | Mw (kg/mol) | PDI | Quantity (mg) | Expected Yield (100% recovery) (mg) |
|---|---|---|---|---|---|---|---|---|
| poly (propylacrylic acid) | | | −5.734 | 1.28 | 7 | 1.4 | | |
| poly (propylacrylic acid)-g-1 mol % PEG2000 | 1 | 4 | −3.479 | 0.594 | 73 | 1.4 | 50 | 230 |
| poly (propylacrylic acid)-g-5 mol % PEG2000 | 5 | 6 | −3.215 | 0.517 | 60 | 1.6 | 50 | 370 |
| poly (propylacrylic acid)-g-10 mol % PEG2000 | 10 | 9 | −3.29 | 0.545 | 94 | 1.4 | 50 | 550 |
| poly (propylacrylic acid)-g-25 mol % PEG2000 | 25 | 12 | −2.56 | 0.362 | 85 | 1.8 | 90 | 1080 |
| poly (propylacrylic acid)-g-1 mol % PEG5000 | 1 | 5 | | | 51 | 1.4 | 250 | 286 |
| poly (propylacrylic acid)-g-5 mol % PEG5000 | 5 | 20 | | | 55 | 1.4 | 220 | 634 |
| poly (propylacrylic acid)-g-10 mol % PEG5000 | 10 | 21 | | | 57 | 1.4 | 320 | 1000 |
| poly (propylacrylic acid)-g-25 mol % PEG5000 | 25 | 35 | | | 55 | 1.5 | 700 | 2380 |
| poly (propylacrylic acid)-g-1 mol % JEFFAMINE® 2000 | 1 | 10 | −3.533 | 0.644 | 69 | 1.4 | 20 | 235 |
| poly (propylacrylic acid)-g-5 mol % JEFFAMINE® 2000 | 5 | 26 | | | 43 | 1.9 | 30 | 370 |
| poly (propylacrylic acid)-g-10 mol % JEFFAMINE® 2000 | 10 | 25 | −3.841 | 0.627 | 58 | 1.9 | 60 | 550 |
| poly (propylacrylic acid)-g-25 mol % JEFFAMINE® 2000 | 25 | 38 | −3.073 | 0.478 | 71 | 2.1 | 200 | 1080 |
| poly (acrylic acid) | | | −2.775 | 0.503 | 104 | 1.2 | | |
| poly (acrylic acid)-g-5 mol % PEG2000 | 5 | 3 | −2.624 | 0.472 | 416 | 1.2 | 50 | 250 |

1.6 Graft Polymer Solubility Studies:

The PPAA copolymers of the present invention were assessed for solubility in 10% by volume 1N NaOH (pH 14) or 90% by volume of pH 7.4 phosphate buffer. Results are shown in Table 3 below.

TABLE 3

Summary of Solubility Data

| Molecular Weight | % grafting density | Solubility in Phosphate buffer (pH 7.4) (Did not solubilize in NaOH formulation since ester bonds break, yielding PEG + PPAA) |
|---|---|---|
| PEG 2K-PPAA | 1 | No |
| PEG 2K-PPAA | 5 | No |
| PEG 2K-PPAA | 10 | No |
| PEG 2K-PPAA | 25 | No |
| PEG 5K-PPAA | 1 | No |
| PEG 5K-PPAA | 5 | No |
| PEG 5K-PPAA | 10 | Yes |
| PEG 5K-PPAA | 25 | Yes |

| Molecular Weight | % grafting density | Solubility in NaOH & Phosphate buffer (pH 12:pH 14:pH 7.4 = 2:1:3.67) net pH of solution: 12.5 |
|---|---|---|
| JEFFAMINE® 2K-PPAA | 1 | Yes |
| JEFFAMINE® 2K-PPAA | 5 | Yes |
| JEFFAMINE® 2K-PPAA | 10 | Yes |
| JEFFAMINE® 2K-PPAA | 25 | No |

1.7 Graft Polymer Complexation Studies:

PPAA-JEFFAMINE® copolymers of various percent grafting density according to the present invention were used to prepare complexes of 1,2-Dioleoyl-3-Triethylammonium Propane (DOTAP)/PPAA-JEFFAMINE®/Oligodeoxynucleotide (ODN). Addition of PPAA-JEFFAMINE® 2000 10 mol % copolymers to DOTAP/ODN complexes caused higher release of ODN compared to addition of PPAA polymer alone. As shown in FIG. 4b, addition of PPAA-JEFFAMINE® 2000 5 mol % copolymers to DOTAP/ODN complexes caused higher release of ODN compared to addition of PPAA-JEFFAMINE® 2000 1 mol % copolymer.

1.8 Graft Polymer Uptake and Delivery Studies:

A therapeutic delivery system comprising instant graft copolymers was assessed using Chinese Hamster Ovary (CHO) cells stably expressing Green Fluorescent Protein (GFP). PS ODN 157, an anti-GFP target sequence with a phosphorothioate backbone, was administered in a transfection system of serum-containing media (8% FBS). Uptake (a.f.u.) data was indicative of the levels of fluorescently tagged PS ODN inside the cells, while % Fluorescence (GFP) data was indicative of the GFP fluorescence of 10,000 cells. Analyses were performed at 24 hours post-transfection.

Levels of PS-ODN uptake for DOTAP/ODN (N/P=4.7) were very low. The addition of anionic polymer PPAA increased uptake only moderately. However, addition of copolymer PPAA-JEFFAMINE® 2000 10 mol % copolymer significantly increased uptake (10 fold) @ N/P=0.5. No antisense silencing effect was observed with the DOTAP/ODN (N/P=4.7) system. Addition of PPAA polymers reduced GFP expression by only 20% @N/P=1. However, addition of PPAA-JEFFAMINE® 2000 10 mol % copolymer to DOTAP/ODN reduced GFP expression significantly (—80%). The maximum shut off of expression occurs @ N/P=0.5.

PPAA-PEG 5000 (10 mol % or 25 mol %) copolymers in DOTAP/ODN complexes showed similar results. No antisense silencing effect was observed with the DOTAP/ODN/PPAA-PEG 5000 complexes.

JEFFAMINE® conjugated to PPAA in DOTAP/ODN complexes showed similar results. Table 4 summarizes uptake and percent fluorescence results for scrambled ODN and Table 5 presents uptake and percent fluorescence results for grafted polymers DOTAP/ODN.

TABLE 4

Uptake and percent fluorescence results for scrambled ODN.

|  | % Green Fluorescence | stdev | uptake of Cy5-ODN | stdev |
|---|---|---|---|---|
| D/O157(4.7) | 103.0 | 3.4 | 150.1 | 27.4 |
| D/Oscrambled(4.7) | 113.2 |  | 128.9 |  |
| D/O157/PPAA(1) | 87.1 | 7.8 | 243.4 | 151.8 |
| D/Oscrambled/P(1) | 94.9 |  | 436.9 |  |
| D/O157/J2K 5 mol %-P(0.5) | 17.5 | 3.2 | 1874.0 | 546.7 |
| D/Osc/J2K 5 mol %-P(0.5) | 123.9 | 22.7 | 1537.2 | 336.0 |
| D/O157/J2K10 mol %-P(0.5) | 18.1 | 0.6 | 1646.1 | 157.3 |
| D/Osc/J2K10 mol %-P(0.5) | 58.3 |  | 1544.0 |  |

TABLE 5

Uptake and percent fluorescence results for grafted polymers by themselves

| Description |  | N/P | % Green Fluorescence | Uptake Cy5-ODN |
|---|---|---|---|---|
| J2K1 mol %-P | polymer only | 0.5 | 94.0 | 1.0 |
| J2K5 mol %-P | polymer only | 0.5 | 96.0 | 1.0 |
| J2K10 mol %-P | polymer only | 0.5 | 94.4 | 1.0 |

As is evident from Tables 4 and 5, (DOTAP/ODN/PPAA-JEFFAMINE®), but not JEFFAMINE® polymer (DOTAP/ODN/PPAA+JEFFAMINE®) by itself in the DOTAP/ODN complexes induced the enhanced antisense effect under serum conditions.

Example 2

Using Graft Copolymers for Delivery of Antisense Oligonucleotides in the Presence of Serum Materials. A phosphorothioate oligodeoxynucleotide tagged with Cy5 (5'-/5Cy5/TTG TGG CCG TTT ACG TCG CC-3' (SEQ ID NO: 1)) was used for physical and biological studies. The 20-mer oligonucleotide (ODN) (EGFP157), previously selected for down regulation of d1EGFP, was used to assess the degree of silencing or antisense effect. We have confirmed that the presence of the Cy5 tag does not significantly alter the delivery of ODNs into cells or the ability of ODNs to bind with mRNA and achieve an antisense effect. The ODNs were obtained from Integrated DNA Technologies (Coralville, Iowa) and delivered as HPLC grade. Before use, lyophilized ODNs were resuspended in phosphate buffer saline (PBS) (Invitrogen, Carlsbad, Calif.) solution of pH 7.2 to a concentration of 100 µM.

The cationic liposomal formulation, N-[1-(2,3-dioleyloxy)propyl]-N,N,N-trimethylammonium methyl sulphate (DOTAP), was purchased from Roche Applied Science (Indianapolis, Ind.) in a liposomal form. Lipofectamine-2000 was purchased from Invitrogen and used as directed. Poly(α-propylacrylic acid) (PPAA) (Mn=27 kDa) was purchased from Polymer Source (Montreal, Canada). PEO monomethyl ether (MW=5 kDa) was purchased from Fluka. 1-(3-dimethylamino-propyl)-3-ethyl-carbodiimide was purchased from Kawaguchi Chemical Industry Co., Ltd. (Tokyo, Japan). 4-(dimethyl-amino) pyridinium 4-toluenesulfonate was synthesized following a published procedure. JEFFAMINE® M-2070 (MW=2 kDa, EO/P0=31/10) was obtained from Huntsman International, LLC (Woodlands, Tex.).

For characterization studies, PPAA polymer, which was received as a dried powder, was solubilized in 0.1 N NaOH in PBS (pH 13). The JEFFAMINE® M-2070 grafted PPAA copolymer (PPAA-g-JEFFAMINE®) was solubilized in a NaOH—PBS (pH 12.5) formulation and then diluted. The PEO grafted PPAA copolymer (PPAA-g-PEO) was solubilized in PBS (pH 7.4). Solutions of DOTAP, ODN and polymers were stored at 4° C. and vortexed prior to use. All other reagents and solvents were purchased from Sigma-Aldrich (St. Louis, Mo.), unless noted otherwise. All buffers were prepared in MilliQ ultrapure water and filtered (0.22 µm) prior to use.

2.1 Synthesis of Graft Copolymers

Methods described in Moore, J., Stupp, S I. *Journal of Organic Chemistry* 1990, 55, 3374 and Hourdet D, L. A. F., Audebert R. *Polymer* 1997, 38, 2535-2547 were followed. This reference is incorporated by reference herein in its entirety.

For the PPAA-g-PEO copolymer, 200 mg PPAA was added to 5 mL DMSO along with 11 mg DPTs, and a slight molar excess of PEO monomethyl ether required to achieve the target graft ratio. The mixture was stirred for 30 min at room temperature, after which 41 mg of EDCI was added. The reaction was allowed to proceed at room temperature and driven to completion by the addition of subsequent 100 mg aliquots of EDCI added on days 4, 9, and 11. The reaction mixture was then transferred to a Slide-A-Lyzer cassette with 10 kDa cut off and exhaustively dialyzed against deionized water. The dialyzed solution was then lyophilized.

For the PPAA-g-JEFFAMINE® copolymer, the same synthesis, dialysis and lyophilization protocols that were used for PPAA-g-PEO copolymer were followed, with the exception that JEFFAMINE® M-2070 replaced the PEO monomethyl ether and HOBt was used as the catalyst in place of DPTs.

Conventional gel permeation chromatography was used to monitor the progress of the reactions and as an indicator of the final molecular weight and polydispersity of the graft copolymers. This was performed with the Waters 510 HPLC unit equipped with a Waters 410 Differential Refractometer, a 5 μm PL gel precolumn, and two PL gel columns (pore size $10^3$-$10^5$ Angstroms) that have been calibrated with polystyrene standards by using DMF containing 0.1% trifluoroacetic acid as the mobile phase at a flow rate of 0.8 mL min$^{-1}$.

2.2 Delivery Complex Preparation:

The delivery complexes are self-assembled from their components through electrostatic interactions, first between the cationic DOTAP liposomes and anionic ODN, and then between the DOTAP/ODN complexes and the anionic polyelectrolytes (PPAA, PPAA-g-PEO or PPAA-g-JEFFAMINE®). Complexes were prepared using a DOTAP/ODN weight ratio of 10:1, which corresponds to a charge ratio of 4.7 (+/−). The calculated net charge ratio is defined as the ratio of the moles of DOTAP amine groups to the sum of the moles of ODN phosphate groups and PPAA carboxylic acid groups. The DOTAP working concentration used was 20 μg/ml. For the ODN encapsulation assay, complexes were formed in PBS to yield a final ODN concentration of 750 nM. For gene silencing experiments, complexes were formed in PBS to yield a final ODN concentration of 300 nM. All DOTAP/ODN/polyelectrolyte complexes were formed by mixing equal volumes of DOTAP and ODN, followed by incubation for 30 minutes at room temperature. Polyelectrolyte was then added to the DOTAP/ODN solution to produce the desired charge ratio. DOTAP and ODN were assumed to be completely ionized (100%), while the carboxylic acids of PPAA were assumed to be 33% ionized at pH 7.4 based on its pKa value. This assumption made for PPAA was also applied to the remaining PPAA groups in PPAA-g-PEO and PPAA-g-JEFFAMINE® copolymers. LipofectAMINE 2000 (Invitrogen, Carlsbad, Calif.) complexed to ODN in a weight ratio of 2:1 was employed as a control. The ratio of complex volume to buffer/media volume was maintained constant at 1:4.

2.3 Cell Culture.

Chinese hamster ovary (CHO-K1) cells stably integrated with destabilized EGFP (d1EGFP) transgene were prepared as known in the art. A glioblastoma (U87) cell line (ATCC, Manassas, Va.) also expressing d1EGFP was developed in a similar manner by transfecting these cells with the 4.9-kb pd1EGFP-N1 plasmid (BD Biosciences Clontech, Palo Alto, Calif., USA), followed by clonal selection and maintenance under selective pressure of G418 (Invitrogen, Carlsbad, Calif.). The CHO-d1EGFP cell line was maintained in F-12K medium (Kaighn's modification of Ham's F-12; ATCC, Manassas, Va.) supplemented with 10% fetal bovine serum (FBS) (Invitrogen, Carlsbad, Calif.), 100 U/mL penicillin (Invitrogen, Carlsbad, Calif.) and 100 μg/mL streptomycin (Invitrogen, Carlsbad, Calif.). The U87-d1EGFP cell line was maintained in 10% Minimal Essential Media (MEM) (ATCC, Manassas, Va.) supplemented with 10% FBS, 4 mM L-glutamine (Invitrogen, Carlsbad, Calif.), 1 mM sodium pyruvate, 1 mM non-essential amino acids, 100 U/mL penicillin and 100 μg/mL streptomycin. Both cell types were maintained under constant selective pressure by using G418 antibiotic (500 μg/ml). Cells were cultivated in a humidified atmosphere at 5% $CO_2$ and 37° C.

2.4 Characterization of PPAA-g-PEO and PPAA-g-JEFFAMINE®:

The extent of PEO and JEFFAMINE® M-2070 grafting onto PPAA backbones was determined by NMR spectroscopy, which was performed on a Varian 400 MHz spectrometer. The percentage of grafting was calculated by the ratio of the integrated peak areas of the methylene protons in the grafted chains to the methyl protons in PPAA. For the PPAA-g-PEO, $^1$H NMR (DMSO-$d_6$) δ 0.80 (s, $CH_3$), 0.95-2.0 (m, br, $CH_2$(PPAA), 2.10 (br), 2.17 (br), 2.29 (br), 2.35, 2.41, 2.64, 2.77, 2.9-3.3 (br), 3.2 ($OCH_3$), 3.29 (t), 3.47 (s, —$OCH_2CH_2O$—), 3.65 (t), 4.10 (br, C(O)$OCH_2CH_2OPEO$), 4.6-4.8 (br), 4.9-5.2 (br), 7.05 (br), 8.45 (br). For the PPAA-g-JEFFAMINE®, $^1$H NMR (DMSO-$d_6$) δ 0.82 (s, $CH_3$), 1.0-2.0 (br, $CH_2$), 2.10, 2.17, 2.2-3.0 (br), 2.9-3.0 (br), 3.2 ($OCH_3$), 3.24-3.42 (m, $CH+CH_2$ (PPO), 3.47 (s, —$OCH_2CH_2O$—), 3.50, 3.51, 3.52, 3.65 (t), 4.6-4.8 (br), 5.0-5.3 (br), 5.50 (s), 7.08 (d), 7.45-7.60 (br), 7.66 (C(O)NH).

The NMR spectra of PPAA-g-PEO copolymer contain chemical shifts expected for methylene protons of the PEO ester moiety formed by reaction of the PPAA carboxylic acids with the primary alcohol of PEO (4.1 ppm). In the case of PPAA-g-JEFFAMINE®, the spectra contain the amide proton (NH) that is formed by reaction of PPAA carboxylic acid groups with the primary amine of JEFFAMINE® (7.6 ppm). The GPC chromatograms of the isolated products also reveal the disappearance of the starting materials and the appearance of new multimodal peaks at high molecular weight.

Because only a few of the graft copolymers from the initial set synthesized were soluble in aqueous buffer, even when NaOH base was added to enhance solubility, the physical and biological studies were limited to investigations of two similar graft copolymers: 1) PPAA-g-PEO containing 21 mole % grafting of the 5 kDa PEO monomethyl ether, total number-average molecular weight of 57 kDa, and polydispersity index of 1.4; and, 2) PPAA-g-JEFFAMINE® containing 25 mole % grafting of the 2 kDa JEFFAMINE® M-2070, total number-average molecular weight of 58 kDa, and polydispersity index of 1.9. These graft copolymers are not completely analogous, as the pendent comb chains of PEO are of greater molecular weight than the pendent JEFFAMINE® chains. Nevertheless, these two graft copolymers provide us with sufficient structural similarities to allow comparisons of their abilities to deliver ODN to cells in the presence of serum-containing treatment conditions.

2.5 Physical Characteristics of DOTAP/Polymer/ODN Complexes:

The degree of ODN encapsulation in the vectors was determined by measuring the quenching of fluorescence from Cy5 labeled ODNs (F-ODNs). Solutions of DOTAP/F-ODN in the presence and absence of PPAA or PPAA graft copolymers were loaded into a polystyrene clear bottom 96-well black plate (Corning, Corning, N.Y.). The Cy5 fluorescence intensity was measured at excitation and emission wavelengths of 630 and 680 nm, respectively, using an Ascent Fluorescence Multi-well Plate Reader. After background subtraction each data point was normalized to control, i.e., uncomplexed ODN. Disruption of the complexes to recover encapsulated F-ODN was achieved by using a 0.25% solution of Triton X-100. Negligible fluorescence (close to background) was obtained for carrier (in the absence of ODN) and Triton X-100 (in the absence of ODN). The degree of encapsulation in the presence and absence of Triton X-100 was calculated by the following formula:

$$\% \text{ Encapsulation} = \frac{(F_{680,sample} - F_{680,PBS})}{(F_{680,ODN} - F_{680,PBS})} * 100$$

In this binding study, the charge ratio of DOTAP/ODN was fixed at 4.7 (corresponding to a weight ratio of 10/1), and the net charge ratio of complexes containing anionic PPAA or graft copolymers was 1.0. The degree of ODN binding in the various complexes was quite similar, with less than 20% free ODN detected either in the presence or absence of polymer. Further, the encapsulated ODN was recovered when the complexes were disrupted with Triton X-100 surfactant. Fluorescence (Cy5) corresponds to free Cy5-ODN in solution, while absence of fluorescence indicates quenching or ODN in bound (complexed) state. These results demonstrated that the binding ability of the cationic liposome, DOTAP, with anionic ODN is unaltered by the addition of PPAA or graft copolymers, and furthermore that the ODN was still part of the complexes and could be recovered.

To further characterize the complexes, particles were examined using dynamic light scattering. Particles sizes were measured at a DOTAP/ODN charge ratio of 4.7 and a DOTAP/ODN/polyelectrolyte net charge ratio of 1 in PBS, Opti-MEM (serum-free media) and MEM (containing 10% FBS). The particle sizes of DOTAP/ODN complexes in the absence of polymer were smallest in PBS solution, compared to opti-MEM or MEM with 10% FBS. The particle sizes of all the other complexes containing PPAA, PPAA-g-PEO or PPAA-g-JEFFAMINE® were found to be independent of the buffer solution. In general, all of the complexes formed fairly stable particles in the three buffer solutions with sizes ranging from 215-300 nm. Overall, these observations were in agreement with the results from the ODN encapsulation studies, where all the complexes bound to ODN equally efficiently. Further, they indicated that neither PPAA nor its graft copolymers induced widespread aggregate formation, despite the overall charge neutrality of the system.

2.6 Hemolysis

The membrane-disruptive activity of PPAA and the grafted polymers was assessed using a hemolysis assay as described in Murthy, N.; Robichaud, J. R.; Tirrell, D. A.; Stayton, P. S.; Hoffman, A. S. *J Control Release* 1999, 61, 137-143. Stock solutions of polymers were vortexed thoroughly to ensure complete solubility, and dilutions of the polymer were prepared fresh. Phosphate buffers, in the pH range 5.5-7.0, and citrate buffer of pH 5.0, were prepared by titration of 100 mM sodium mono and diphosphate and 100 mM sodium citrate, respectively, to achieve the appropriate pH values. Solutions of PPAA, PPAA-g-PEO and PPAA-g-JEFFAMINE® were added to pH buffers 5.0, 5.5, 6.0, 6.5 and 7.0 at 40, 240 and 400 μg/ml and vortexed thoroughly. To these polymer solutions, fresh RBCs that had been washed just prior three times with 100 mM NaCl were added at $10^8$ cells/ml, incubated in a water bath at 37° C. for 1 hr, and then centrifuged for 4 mM and 400 g to pellet the intact RBCs. The absorbance of the supernatants (541 nm) was determined on a UV spectrophotometer (Thermo Spectronic). Experimental controls included RBCs in pH buffers in the absence of polymer (negative control) and RBCs in distilled water (positive control). Each test was performed in triplicate. The percentage of hemolysis was determined using the formula below:

$$\text{Hemolysis} = \frac{(A_{541,sample} - A_{541,buffer})}{(A_{541,distilledwater})} * 100$$

RBC hemolysis induced by polymer was normalized to control (distilled water). PPAA produces significant hemolytic activity at pH 6.0, the pH of endosomes, and absence of hemolytic activity at pH 7.0, the pH of the cytoplasm. In comparison, both the graft copolymers, PPAA-g-PEO and PPAA-g-JEFFAMINE®, demonstrated <10% hemolytic activity throughout the pH range of 5.0 to 7.0.

2.7 Intracellular ODN Delivery and Inhibition of d1EGFP Expression.

The biological activity of the ODN complexes was assessed in CHO and U87 cell lines that stably express a target gene encoding d1EGFP, a form of enhanced green fluorescent protein with a protein half-life of approximately 1 hr. The intracellular delivery of ODN molecules into cells and the gene silencing effects were quantitatively determined from the fluorescence of Cy5-labeled ODN and GFP expression, respectively, using flow cytometry.

Cells were split at approximately 70% confluence and seeded onto 12-well plates (Fisher, Suwanee, Ga.) at $10^5$ cells/ml (with 1 ml per well) ~18 h prior to ODN treatment. For cellular uptake and antisense studies, cells were treated with Cy5-labelled antisense ODN (target d1EGFP gene encoding GFP) to result in a final ODN concentration of 300 nM per well. In the case of treatment, 200 μl of complexes were prepared as described in the 'Vector preparation' section, mixed with 10% serum-containing cell culture medium and added to each well, while for the control samples complexes were substituted with 200 μl of PBS. After 4 hours of cell exposure to treatment, complexes were aspirated and cells were refilled with fresh medium. Cells were assayed for Cy5-ODN uptake and GFP activity 24 hrs post-ODN treatment using fluorescence activated cell sorting (FACS).

Cells were prepared for FACS analysis first by washing cells with PBS buffer, followed by the addition of trypsin-EDTA (Invitrogen, Carlsbad, Calif.) to remove cells from the plate surface Immediately after cell detachment, cell culture medium was added to neutralize the trypsin. Following this, cells were collected in pellet form by centrifugation for 3.5 min at 200 g, resuspended in 150 μl of PBS and maintained on ice until the time of analysis. Cells were analyzed for size (side scatter), granularity (forward scatter), intensity of Cy5 fluorescence (FL4 channel) and intensity of GFP (FL1 channel). Geometric mean fluorescence intensities for 10,000 cells were determined on the FACS Calibur three-laser flow cytometer (BD Biosciences). "Control" refers to DOTAP/ODN only and other groups indicate the polymer added to this combination, except "lipo" refers to delivery with Lipofectamine-2000. CellQuest software was used to acquire and analyze the results. After ensuring that the background GFP fluorescence from cells lacking d1EGFP plasmid was negligible, the degree of silencing was calculated using the following formula:

$$\% \text{ Silencing} = \frac{(F_{525,treatment})}{(F_{525,control})} * 100$$

Figure 4A:
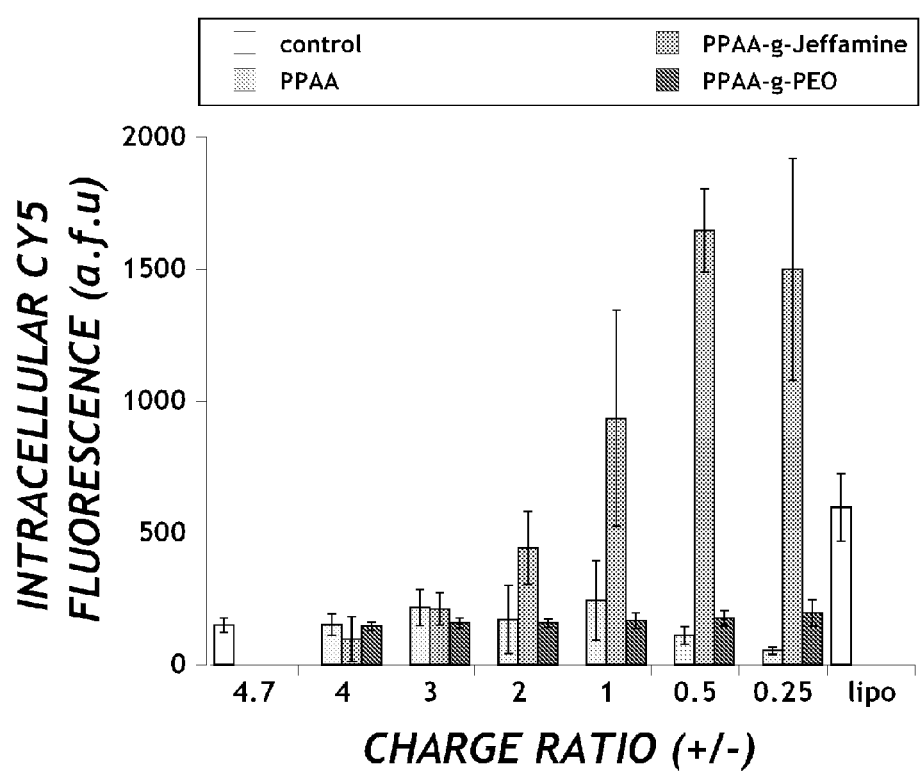
FIGS. 4a and 4b present results of studies on cellular uptake and antisense activity, respectively, of DOTAP/ODN complexes in the presence of PPAA, PPAA-g-JEFFAMINE® or PPAA-g-PEO in CHO-d1EGFP cells 24 hours post-treatment.
Figure 4B:
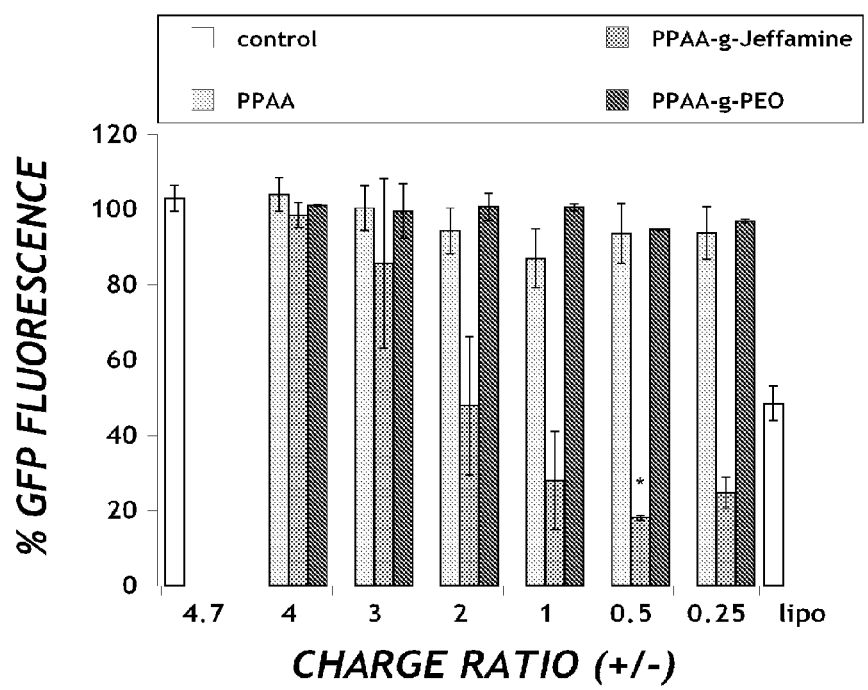

The results for CHO-d1EGFP cell line are presented in FIGS. 4a and 4b. The % GFP Fluorescence was normalized to untreated cells.

In 10% serum-containing media, relatively low levels of Cy5-ODN uptake and minimal antisense activity by the DOTAP/ODN/PPAA complex over a range of charge ratios from 4.7 to 0.25 was observed. The incorporation of PPAA-g-PEO copolymer into DOTAP/ODN complexes also produced no substantial increase in intracellular ODN levels, yielding insignificant antisense activity throughout the range of charge ratios tested. In marked contrast, complexes containing PPAA-g-JEFFAMINE® copolymer produced an 8-fold increase in intracellular levels of ODN compared to PPAA, under the same 10% serum-containing conditions. This enhanced uptake with the PPAA-g-JEFFAMINE® correlated with a gene silencing effect of ~90%. Moreover, PPAA-g-JEFFAMINE® containing complexes delivered ODN and produced a greater antisense effect than the commercial standard, Lipofectamine 2000. The maximum ODN delivery and gene silencing effects induced by PPAA containing complexes occurred at a net charge ratio of 1.0, while for PPAA-g-JEFFAMINE® containing complexes the maximum occurred at a net charge ratio of 0.5.

Figure 5A:
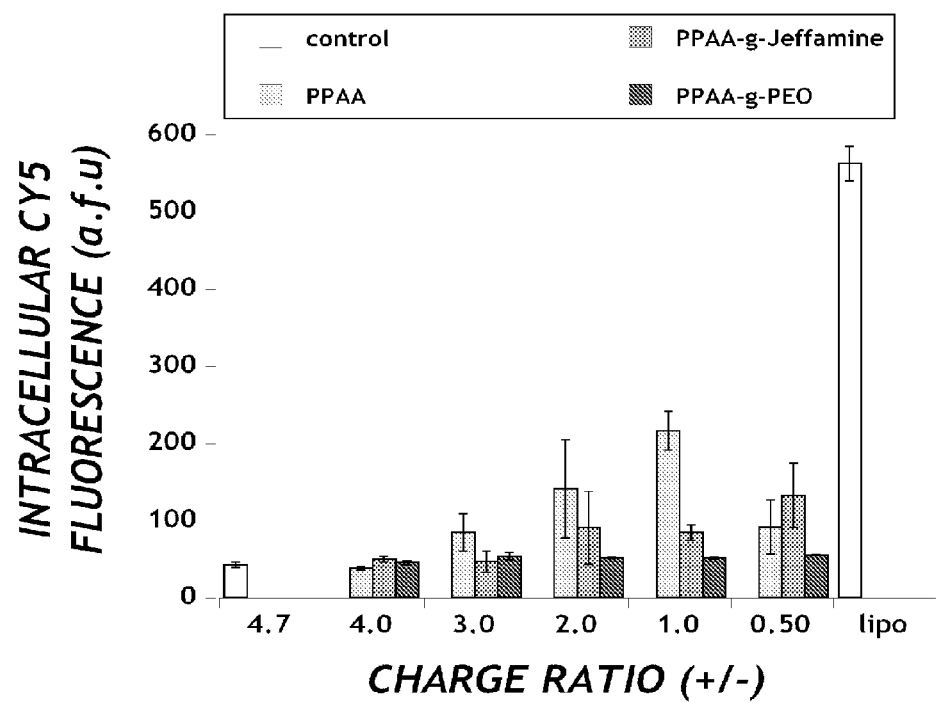
FIGS. 5a and 5b present results of studies on cellular uptake and antisense activity, respectively, of DOTAP/ODN complexes in the presence of PPAA, PPAA-g-JEFFAMINE® or PPAA-g-PEO in U87-d1EGFP cells 24 hours post-treatment.
Figure 5B:
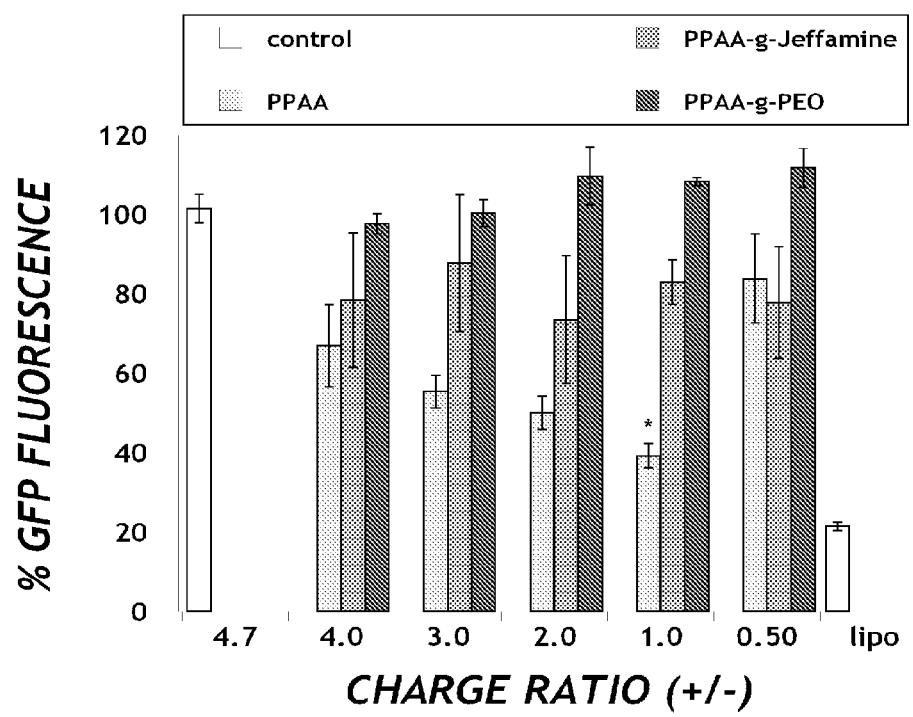

The results for U87-d1EGFP cell line are presented in FIGS. 5a and 5b. In U87-d1EGFP cells, the ability of the various carrier systems to deliver ODN was rather different than that in the CHO-d1EGFP cells. Similar to the results for the CHO-d1EGFP cell line, the DOTAP/ODN delivery system failed to initiate sufficient ODN uptake or significant antisense effect by U87-d1EGFP cells in the presence of serum. In this case, PPAA by itself was the most effective adjunct in treatments with serum-containing media in terms of ODN delivery and gene silencing activity. The PPAA-containing complexes caused a 4-fold increased uptake of ODNs, which resulted in 60% GFP fluorescence level (or 40% gene silencing) compared to control. Here, the maximum ODN delivery into cells occurred at a net charge ratio of 1. In the case of complexes containing PPAA-g-PEO, low levels of intracellular ODN uptake and negligible gene silencing effects were observed. PPAA-g-JEFFAMINE® containing complexes produced a two-fold increased uptake of ODNs compared to complexes without any polymer addition (i.e., DOTAP/ODN), and 30% gene silencing. The PPAA-g-JEFFAMINE® containing complexes achieved maximum antisense activity at a charge ratio of 2, compared to a charge ratio of 0.5 in CHO-d1EGFP cells.

2.8 Cytotoxicity/Cell Proliferation

CHO-d1EGFP cells were seeded onto a 96-well plate and treated with 20 μL of complexes, prepared according to methods described above, and mixed with 80 μL of serum-containing media (10% FBS). After 24 hours, 20 μL of MTT reagent (Promega, Madison, Wis.) was added to 100 μL of media, per the manufacturer's protocol, and cells were incubated for a period of two hours under humidified conditions. Production of the tetrazolium salt (MTT) was quantified colorimetrically to represent cell viability, as follows:

$$\% \text{ Cell Viability} = \frac{A_{490, treatment}}{A_{490, control}} * 100$$

In both CHO-d1EGFP and U87-d1EGFP cell lines the greatest cytotoxicity was induced by the complex that yields highest ODN delivery and antisense activity. That is, in CHO-d1EGFP cells, the PPAA-g-JEFFAMINE® containing complex was the most cytotoxic at the optimal charge ratio of 0.5, although the effect was relatively small (cell viability exceeds 80%). Similarly, in U87-d1EGFP cells, the PPAA containing complex was the most cytotoxic (cell viability reduced to about 50%) at the optimal charge ratio of 1.0.

Example 3

Silencing of Oncogene Expression in Cancer Cells by Delivery of siRNA with Graft Copolymer Formulation The ability of graft copolymers to enhance cationic liposome-mediated delivery of siRNAs that is targeted to Bcl-2, anti-apoptotic, gene was tested. The degree of Bcl-2 gene silencing was assessed in HeLa (cervical carcinoma) and MCF-7 (breast cancer) cell lines that over-expressing this oncogene.

Cells were seeded in 12-well plates at ~$10^5$ cells/ml and treated with siRNA-containing complexes (at a final siRNA concentration of 40 and 50 nM) 20 hours post-seeding. The cells were treated with complexes for a period of 4 hours under serum-containing (10% FBS) media, after which complexes were aspirated and replaced with fresh media. We evaluate the degree of mRNA gene silencing 24 hours post-treatment using PCR (polymerase chain reaction) by the 2ΔΔ$C_T$ method. This method assumes equal amplification efficiencies for b-actin and Bcl-2 gene.

The degree of gene silencing was calculated using the following equations:

$$\Delta C_T = (C_T)_{Bcl\text{-}2} - (C_T)_{\beta\text{-}actin}$$

$$\Delta\Delta C_T = (C_T)_{treatment} - (C_T)_{control}$$

$$\% \text{ Silencing} = 100 - (2^{-\Delta\Delta C_T} * 100)$$

The degree of gene silencing in HeLa cell type (cervical carcinoma) observed 24 hours after treatment with siRNA at concentration of 40 nM using various siRNA delivery methods are presented in Table 6 below.

TABLE 6

The degree of gene silencing in HeLa cell type

| Sample | $(C_T)_{\beta\text{-}actin}$ | $(C_T)_{Bcl\text{-}2}$ | $\Delta C_T$ | $\Delta\Delta C_T$ | % Silencing |
|---|---|---|---|---|---|
| Control | 11.9 | 25.6 | 13.6 | | |
| Lipofectamine 2000/siRNA | 11.8 | 26.2 | 14.4 | 0.8 | 42.6 |
| DOTAP/PPAA/ siRNA | 12.4 | 27.0 | 14.5 | 0.9 | 46.0 |
| DOTAP/PPAA-g-JEFFAMINE ®/ siRNA | 12.1 | 27.1 | 15.0 | 1.4 | 61.0 |

The degree of gene silencing in MCF-7 cell type (breast tumor) observed 24 hours after treatment with siRNA at concentration of 50 nM using various siRNA delivery methods are presented in Table 7 below.

TABLE 7

The degree of gene silencing in MCF-7 cell type

| Sample | $(C_T)_{\beta\text{-}actin}$ | $(C_T)_{Bcl\text{-}2}$ | $\Delta C_T$ | $\Delta\Delta C_T$ | % Silencing |
|---|---|---|---|---|---|
| Control | 10.2 | 21.9 | 11.6 | | |
| Lipofectamine 2000/siRNA | 10.1 | 21.9 | 11.9 | 0.25 | 15.9 |
| DOTAP/PPAA/ siRNA | 10.3 | 22.0 | 11.7 | 0.1 | 6.0 |
| DOTAP/PPAA-g-JEFFAMINE ®/ siRNA | 10.1 | 22.6 | 12.5 | 0.9 | 46.4 |

Example 4

Cationic Antimicrobial Peptide-Graft Copolymer Complex

4.1 Polymer Synthesis and Characterization

Linear polymers of poly(propylacrylic acid) (PPA) and poly(methacrylic acid) (PMAA) were prepared by standard free radical polymerization under nitrogen using AIBN as the initiator. Their molecular weights were determined by proton nuclear magnetic resonance. ($^1$H NMR) (500 MHz-Varian Inova, Santa Clara, Calif.) and by gel permeation chromatography (GPC) (Malvern Viscotek with Triple Detector, Houston, Tex.) using an A4000 300×7.8 mm column (Malvern, Westborough, Mass.), polystyrene standards, and a mobile phase consisting of dimethylformamide with 0.1% trifluoroacetic acid.

Graft copolymers were then prepared from the PPAA and PMAA backbones and the polyetheramine JEFFAMINE® VR M2070 using carbodiimide coupling as described above. The molecular weights and graft densities of the resulting copolymers were determined by GPC and by $^1$H NMR. Hereafter, the nomenclature used in describing the graft copolymers will be, e.g., PMAAg1, meaning the graft copolymer of PMAA and JEFFAMINE® M2070 was synthesized at a molar ratio of 1:100 (1.0 mol JEFFAMINE® per 100 mol PMAA carboxylic acid groups).

After lyophilization, each polymer was initially reconstituted in 1-lyclone cell culture-grade water at between 1 and 10 mg/mL and sufficient 1M NaOH to raise the pH to 12.5. This was stirred at room temperature and 500 rpm until the polymer was fully dissolved, adjusting the pH back to 12.5 as needed. The dissolved polymer was dialyzed (5 kDa MWCO) against a large excess of Milli-Q water, using at least three exchanges or until the pH was between 7 and 8. Characterizing data for the polymers is presented in Table 8.

TABLE 8

Poly(alkylacrylic acid) Graft Copolymer Molecular Weights and Graft Densities

| Backbone | Graft density (%) | Mw/Mn (kDa) | Designation |
|---|---|---|---|
| PPAA | 0 | 71/27 | PPAA |
| PPAA | 0.5 | 61/26 | ppAAg1 |
| PPAA | 5.9 | 109/52 | PPAAg10 |
| PMAA | 0 | 122/36 | PMAA |
| PMAA | 1.8 | 162/77 | PMAAg1 |
| PMAA | 5.0 | 289/78 | PMAAg10 |

4.2 Zeta-Potential and Particle Sizing

Zeta-potential and particle size of reconstituted polymers and peptide:polymer nanocomplexes were measured using a Malvern Zetasizer Nano ZS instrument. For zeta-potential measurements, a reuseable dip cell was used and Smoluchowski conditions (spherical particles in low-salt, aqueous solution) were assumed in the automated analysis of the electrophoretic mobility. For sizing measurements, 173° backscattering was chosen as the detection mode and light scattering conditions were optimized by the instrument. Preset instrument algorithms were used to relate Brownian motion correlation function to particle size. All readings were conducted at 25° C. after a 120 s equilibration period.

4.3 Evaluating the Influence of Charge Ratio (CR)

A series of peptide:polymer complexes were formulated at a fixed copolymer concentration of 0.05 mg/mL with increasing amounts of peptide KSL-W. Samples were stirred overnight (500 rpm/room temperature) and then sonicated for 20 min to equilibrate structures Light scattering and zetapotential measurements were performed to evaluate self-assembly behavior as a function of polymer characteristics and peptide:polymer charge ratio (CR). Size and zeta-potential of each sample were measured as described earlier.

4.4 Degradation Rates

Aqueous solutions of the peptide:polymer complexes with various peptide:polymer charge ratios and peptide KSL-W concentrations between 30 and 80 mg/mL were combined 1:1 v/v with human plasma (sodium heparin anticoagulated, Biological Specialty Corporation) and placed in a 37° C. incubator. Fifty microliter aliquots of this mixture were injected at 1 h intervals onto a Prosphere HP C18-300 column, 250×4.6 mm (Grace) mounted on a Waters HPLC system. The injection was loaded onto the column and equilibrated using a 90%/10%/0.1% water/acetonitrile/trifluoroacetic acid mobile phase and then eluted using a continuous gradient up to 70% acetonitrile. Integration of the KSL-W absorbance peak at 280 nm was used to determine peptide concentration in each sample. Every sample was run in parallel with a free-drug control at the same concentration.

4.5 Release Profiles

For each sample to be tested, 4 mL of solution containing 66 mg/ml KSL-W and the appropriate amount of polymer for the desired charge ratio (between 0.05 and 0.1 mg/mL depending on polymer graft density and molecular weight) was prepared and aliquoted into four 8-10 kDa MWCO dialysis membranes (Float-a-Lyzer, Spectrum Laboratories). Each membrane cartridge was placed into 40 mL of MilliQ water at 37° C. with gentle rocking (VWR brand incubating rocker, 50 Hz/15°. At 1, 6, 24, and 120 h, one sample of each type was removed from dialysis. The amount of KSL-W remaining in each cartridge was evaluated at each time point using HPLC.

4.6 Binding Efficiency

Efficiency of binding for each polymer-drug plex was determined using ultrafiltration. Ultrafiltration cartridges with 10 k MWCO (Amicon Microcon Ultrafiltration Filters) were used according to manufacturer's instructions. Briefly, each cartridge was filled with 500 μL of sample and centrifuged at 14 k rpm for 20 min. The filter insert containing complexed drug was inverted in a clean centrifuge tube and centrifuged at 1 krpm for 20 min. The KSL-W content of filtrate and retentate were determined using HPLC as described above.

4.7 Antimicrobial Testing

The minimum inhibitory concentrations (MIC) of KSL-W and its nanocomplexes were measured using the Clinical Laboratory Standards Institute (MI) broth microdilution method. Briefly, two-fold serial dilutions of free or complexed KSL-W solutions were prepared in THB medium at a volume of 200 IL/well in flat-bottom 96-well tissue culture plates (BD Biosciences). Hundred microliter of *Staphylococcus aureus* UAMS-1 (10 CFU/mL) was then added to each well. Plates were incubated overnight at 37° C. and then assessed by turbidity (absorbance at 600 nm). The concentration at which no turbidity was observed was considered the MIC. Each assay was reproduced in triplicate.

4.8 Statistical Analysis

Data are presented as means+/−standard deviation unless otherwise indicated. Where only two conditions were compared, statistical comparisons between samples were examined using Student's t-test. This method was used to evaluate differences between size and zeta-potential of KSLW:PPAA10 in water versus saline conditions and peptide degradation in polymer-complexed versus free peptide. Where multiple conditions were compared simultaneously, one-way ANOVA with Tukey adjustment of the p-values for pairwise comparison was used instead. This method was used to evaluate variations in zeta-potential and logarithm of particle size of the different polymer complexes. To account for different total percentages in the release data, a Wilcoxon rank test was performed on the asymptotics of the release curves to determine differences in the release behavior. p-values <0.05 were considered significant in t tests and Wilcoxon test unless otherwise indicated.

4.9 Degradation of KSL-W in Human Plasma

In 50% human plasma, the KSL-W peptide by itself degrades at a rapid, concentration-dependent rate. The half-life of the peptide is 4 h at an initial KSL-W concentration between 33 and 72 µg/mL and 1 h at an initial concentration between 132 and 330 µg/mL, with near-complete degradation of free KSL-W at 24 h for all initial concentrations tested up to 1 mg/mL. At a peptide:polymer charge ratio of 0.5, the degradation rate of KSLW: PPAAg1 is significantly less than that of the corresponding free peptide at all time points (p<0.01), with only 20% degradation at 4 h and 50% at 24 h. KSL-W complexed with either ungrafted PPAA or PPAAg10, on the other hand, degrades at a rate statistically identical to that of the free drug at the same concentration. When complexed with PPAAg1, KSL-W degradation at 2 and 3 h is statistically identical whether complexed at a charge ratio of 0.5 (KSL-W concentration of 132 or 1.0 (KSL-W concentration of 66 µg/mL), in spite of the much increased degradation rate of the free drug at the higher concentration. PMAAg1 provides similar protection to PPAAg1 up to 4 h (p ~0.2) but degradation at 24 h approaches the level of the free drug PPAAg1, on the other hand, limits degradation to 40% (CR 0.5) and 50% (CR 1) at 24 h.

4.10 KSL-W Binding Efficiency and Release from Complexes

At CR 0.5, the initial binding of KSL-W to PPAAg1 and PPAAg10 is effectively 100%. That is, for both of these peptide:polymer complexes, no free KSL-W passes through the 10 kDa NIWCO ultrafiltration membrane in measurable quantities, indicating essentially complete binding of the cationic peptide to the anionic polymer. Free KSL-W at the same concentration passes through the membrane with better than 95% efficiency even when the membrane is first conditioned with graft polymer, indicating that retention of the peptide is indeed due to binding to the polymer and is not due to interference or clogging of the membrane by the polymer. When the initial charge ratio is increased to 5; however, PPAAg10 retention in the filter was only about 20%, statistically similar to the amount of free drug retained in the filter at this higher KSL-W concentration (p ~0.2). This is indicative of a saturation of the binding of the peptide to the polymer backbone, with excess peptide remaining free in solution uncondensed). The graft copolymer nanocomplexes provide controlled release behavior that is dependent on the graft density. At an initial charge ratio of 0.5, the KSLW:PPAAg10 nanocomplex exhibits burst release behavior with almost 80% KSL-W released within 24 h, while the KSL-W:PPAAg1 nanocomplex at the same 0.5 charge ratio exhibits much slower release behavior, with a cumulative 30% release after 120 h, indicating stronger binding of the peptide to the PPAAg1 polymer. The 8-10 kDa dialysis membrane permitted rapid and complete transport of free KSL-W, as indicated by the release of over 95% within the first 6 h of dialysis, and hence was not responsible for the observed differences in release rates from the nanocomplexes. The release rates of KSL-W from both polymers was statistically different (p<0.05) from the diffusion rate of the free KSL-W, as determined by a nonparametric analysis of the asymptotes of each curve.

4.11 Antimicrobial Activity

With the exception of PPAAg1:KSL-W (CR 0.5), the peptide: polymer nanocomplexes retained between 25% and 100% of the antimicrobial activity of the KSL-W, as demonstrated by their MICs against Staphylococcus aureus UAMS-1 (Table 9). The graft copolymers by themselves had no significant antimicrobial activity at dosages up to 1 mg/mL. Although susceptibility guidelines for KSL-W are not available, the dosages required for efficacy are high relative to currently available antibiotics (e.g., we found the MIC of gentamicin against this S. aureus strain under these conditions to be <3.1 mg/mL). KSL-W has previously been studied primarily against salivary bacteria and C. albicans yeast, 4.34 and based on our data KSL-W may not be a lead cationic peptide candidate against S. aureus. Because cationic antimicrobial peptides often use membrane disruption as one mode of bacterial killing, if not the only one, they are generally considered most clinically effective against gram-negative bacteria. Although recent work has demonstrated KSL-W can have activity against S. epidermidis, future efforts at delivering peptide drugs to S. aureus could include the use of peptides with demonstrated activity against gram positive organisms, such as oritavancin or PGLYRP-1, or combining KSL-W with other antimicrobial agents.

TABLE 9

Minimum Inhibitory Concentrations (MICs) for KSLW and its Graft Copolymer Nanocomplexes at Various Charge Ratios Against Staphyloccocus aureus UAMS-1

| Graft copolymer: Peptide | Charge ratio (CR) | MIC (µg/mL) (S. aureus UAMS-1) | MIC ratio (complexed/free) |
|---|---|---|---|
| KSL-W | NA | 62-153 | 1 |
| KSL-W:PPAA | 0.5 | 125 (62) | 2 |
| | 2.5 | 125 (62) | 2 |
| KSL-W:PPAAg1 | 0.5 | >705 (153) | No activity |
| | 2.5 | 125 (62) | 2 |
| KSL-W:PPAAg10 | 0.5 | 250 (62) | 4 |
| | 5 | 100 (100) | 1 |
| KSL-W:PMAAg1 | 0.5 | 125 (62) | 1 |
| | 2.5 | 125 (62) | 2 |
| | 5 | 100 (100) | 1 |

Numbers in parenthesis are the MICs for KSL-W free drug in the specific test; MIC values varied within about one serial dilution from test to test.

This work has established that poly(alkylacrylic acid) polymers grafted with amphiphilic polyetheramine chains can form stable, protective polyelectrolyte nanocomplexes with cationic antimicrobial peptides such as KSL-W. The binding and release characteristics of the peptides from the nanocomplexes can be controlled by adjusting the graft density, polymer backbone, or charge ratio. Depending on the graft density and charge ratio, these peptide:copolymer nanocomplexes can provide substantial protection to the bound peptides from degradation in human plasma for at least 24 h and can retain at least some of the biological activity of the peptide.

Example 5

Delivery of siRNA Silencing Runx2, Inhibiting Osteogenesis in a Cell Culture Model of Heterotropic Ossification (HO)

5.1 Synthesis and Characterization of Poly(Propylacrylic Acid)-Graft-JEFFAMINE®

The graft copolymers were prepared by carbodiimide coupling of JEFFAMINE® M-2070 pendent chains to the acrylate backbone chain (PPAA). Briefly, for the 1% theoretical JEFFAMINE® graft density copolymer, 100 mg of PPAA ($1.41 \times 10^{-3}$ mmol), 17.5 mg of JEFFAMINE® M-2070 ($8.76 \times 10^{-3}$ mmol), 11.8 mg of HOBt ($8.76 \times 10^{-2}$ mmol) and 2.5 mL of DMF were mixed in a 4 mL glass vial until the solids were completely dissolved. Then 16.8 mg of EDC ($8.76 \times 10^{-2}$ mmol) were added, and the reaction vial was placed in the Polyblock-4 reaction block and stirred at 250 rpm at room temperature for 50 hours. This procedure was repeated for the 10% theoretical grafting by increasing the amounts of JEFFAMINE® and HOBt accordingly. The graft copolymers were purified by equilibrium dialysis using a 12-14 kDa MWCO regenerated cellulose dialysis tube (Cellu-Sep, Seguin, Tex.). The dialysis tube containing 10 mL of the reaction mixture was placed in 500 mL of DMF, and the external dialysate solution was exchanged at 48 h with fresh DMF. After 96 h dialysis withDMF, the dialysis was repeated for another 96 h against methanol. The contents of the dialysis bag were mixed with 10 mL of deionized water. The methanol was allowed to evaporate overnight and the resultant graft copolymer mixture in water was lyophilized 1H NMR analysis was used to determine the experimental graft densities by the ratio of the areas of the $CH_2CH_2$ peak of JEFFAMINE® and the $CH_2$ peak of the backbone chain, and the molecular weights were determined by GPC. $^1$H NMR (DMSO-d6) δ 0.85 (s, CH3 of PPAA), 1.0-2.1 (br, CH2 of PPAA), 1.1 (s, CH3 of PPO), 3.20 (s, OCH3), 3.20-3.45 (m, CHCH2 of PPO), 3.5 (s, OCH2CH2O), 7.6 (s, C(O)NH), 12.0 (s, COOH). The Mw/Mn of PPAA-g-1% JEFFAMINE® and PPAA-g-10% JEFFAMINE® were 67 kDa/28 kDa and 109 kDa/52 kDa, respectively. The experimental graft densities based upon $^1$H NMR analyses were 0.1% and 5.9% for the theoretical PPAA-g-1% JEFFAMINE® and PPAA-g-10% JEFFAMINE®, respectively.

5.2 Cell Culture

Mouse myoprogenitor cells (C2C12; ATCC: CRL-1772t) were cultured in Dulbecco's Modified Eagle's Medium (DMEM; ATCC: 30-2002) supplemented with 10% fetal bovine serum (FBS, Invitrogen, Carlsbad, Calif.), 100 U $mL^{-1}$ penicillin and 100 mg mL streptomycin (Invitrogen, Carlsbad, Calif.) at 37° C. in a humidified atmosphere of 5% CO2 in air. For maintenance and passaging, cells were detached from tissue culture surface using trypsin-EDTA (Invitrogen, Carlsbad, Calif.) at 60-70% confluence and re-cultured at 1:6 split ratio. The cells were cultured at 4000 $cm^{-2}$ seeding density in standard tissue culture flasks (BD Falcont, Franklin Lakes, N.J.).

5.3 Screening siRNA Candidates

Small interfering RNA (siRNA) sequences targeting mouse Runx2 were designed on the basis of thermodynamic considerations, using the RNAstructure algorithms, 12 followed by heuristic pruning to restrict selection to sequences containing no more than three of the same nucleotide in succession and to those containing all four nucleotide bases. The shortlisted siRNA sequences shown in Table 10 were custom synthesized and purchased from Dharmacon (Chicago, Ill.). Nonspecific control siRNA labeled with fluorescent Cy5 dye at the 30 end (AllStars Negative Control siRNA) was purchased from Qiagen Sciences (Germantown, Md.). The control siRNA was validated by the manufacturer to have no homology to any known mammalian gene.

TABLE 10

Candidate siRNAs based on RNAstructure analysis

| siRNA | Sequence |
|---|---|
| S-1 Sense | 5'-CAGACAAGUGAAGAGGUUUU-3' (SEQ ID NO: 2) |
| Antisense | 5'-AACCUCUUCACUUGUCUGUU-3' (SEQ ID NO: 3) |
| S-2 Sense | 5'-GCAUAAAGGGAGAAGCAGUU-3' (SEQ ID NO: 4) |
| Antisense | 5'-CUGCUUCUCCCUUUAUGCUU-3' (SEQ ID NO: 5) |
| S-3 Sense | 5'-AUUGAAGAAGAAGCACACUU-3' (SEQ ID NO: 6) |
| Antisense | 5'-GUGUGCUUCUUCUUCAAUUU-3' (SEQ ID NO: 7) |

C2C12 cells, seeded at 4000 cells per $cm^2$ in 12-well plates, were transfected with each of the three candidate Runx2 specific siRNAs or scrambled siRNA in Opti-MEM reduced serum media (Invitrogen, Carlsbad, Calif.) at a final siRNA concentration of 160 nM using Lipofectamine 2000 (Invitrogen) for 4 hours. Cells were cultured in 100 ng mL__1 human recombinant bone morphogenic-2 protein (hrBMP-2) supplemented complete growth media after transfection to induce osteoblastic differentiation, or they were cultured in normal growth media post transfection in case of control. Three siRNAs were tested against the target gene Runx2, and the siRNA with the most potent and specific gene silencing effect was selected for further studies. The cells were assayed for the activity of alkaline phosphatase enzyme on day 3 post-BMP-2 treatment.

5.4 SiRNA Treatment of C2C12 Cells with Nanocomplexes

Appropriate volumes of the cationic liposome DOTAP (Roche Applied Science, Indianapolis, Ind.) and siRNA to achieve a weight ratio of 10:1 (charge ratio (+/−) of 3.8) were first diluted in HBS and PBS buffers respectively as per the manufacturer's guidelines and then complexed by vortex mixing, followed by incubation for 30 minutes at room temperature. The anionic polyelectrolyte (PPAA, PPAA-g-1% JEFFAMINE® or PPAA-g-10% JEFFAMIN®) was added to the DOTAP-siRNA complex to produce a theoretical net charge ratio (+/−) of 1.0, which we have found to be optimal for antisense oligonucleotide delivery, 10 d and the ternary complexes were incubated for an additional 30 minutes at room temperature. Theoretical charge ratios on nano-complexes were calculated by assuming 100% ionization for DOTAP and siRNA and 33% protonation of carboxylic acids in PPAA at physiological pH. Lipofectamine 2000, used as the control delivery agent, was complexed with siRNA at the optimal weight ratio of 2:1 per manufacturer's instructions.

For transfection, the C2C12 cells were cultured in 12 well plates, and siRNA was used at a concentration of 160 nM siRNA. Twenty four hours post-seeding, the conditioned media was removed, and the cells were washed with the fresh media. Next the cells were incubated with the DOTAP/siRNA/polyelectrolyte complexes in the growth media containing 10% FBS for 4 hours. Subsequently, the transfection mixture was replaced by growth media supplemented with 100 ng $mL^{-1}$ BMP-2. The cells were grown for 3-5 days in BMP-2 supplemented media, which was changed every 48 hours.

5.5 Physical Characterization of Nanocomplexes

The complexes were self-assembled in PBS as described above. Hydrodynamic sizes and zeta potentials of the complexes were measured immediately after the formation of the DOTAP/siRNA/polyelectrolyte complexes using a Malvern Instruments Zetasizer Nano ZS-90 instrument (Southboro, Mass.). Dynamic light scattering (DLS) measurements were performed at a 901 scattering angle at 37° C. Each recorded data value was the average of three (for hydrodynamic diameter) and ten (for zeta potential) scans per measurement.

5.6 Cellular Uptake of Nanocomplexes by C2C12 Cells

C2C12 cells were treated with nanocomplexes as described above, using Cy5 labeled negative control siRNA. Cells were analyzed for Cy5-siRNA uptake 24 hours following transfection using fluorescence activated cell sorting (FACS) and laser-scanning confocal microscopy. Geometric mean Cy5 fluorescence (FL4 channel) intensity for 10 000 cells was recorded on the FACS Calibur three-laser flow cytometer (BD Biosciences, San Jose, Calif.). CellQuest software equipped with the flow cytometer was used for the data analysis.

For confocal microscopy, cells were seeded and transfected in the Lab-tekt Chamber Slidet system (Nunc Brand Products, Rochester, N.Y.) at 24 hours post seeding. After four hours of incubation, the transfection mixture was removed and the cells were fixed using 4% paraformaldehyde. DAPI (Invitrogen, Carlsbad, Calif.) and CellMaskt Deep Red (Invitrogen) stains were used to stain nucleus and plasma membrane respectively as per the manufacturer's guidelines. The cell samples were then analyzed using a Leica TCS SP2 laser-scanning confocal microscope (Leica Microsystems Inc, Buffalo Grove, Ill.).

5.7 Runx2 Gene Expression Measurement

The expression of Runx2 gene was measured by quantitative real-time PCR (rtPCR). Total RNA was extracted from the cell samples using an RNeasy Mini kit (Qiagen, Valencia, Calif.), and the cDNA templates were transcribed using RetroScript reverse transcription kit (Ambion, Austin, Tex.) according to the manufacturer's instructions. NanoDropt (Thermo Scientific, Wilmington, Del.) was used to determine the concentration and purity of the RNA preparations. SYBR Green master-mix (Qiagen) was used in RT-PCR reactions according to the manufacturer's instructions, and the reactions were performed in a Lightcycler 3.5 Real-Time PCR System (Roche Diagnostics, Indianapolis, Ind.). All primers were designed in our lab and synthesized by Integrated DNA Technologies, Inc. (IDT, Coralville, Iowa). The Comparative Ct (DDCt) method was used to calculate the relative gene expression levels, where DDCt corresponds to the cycle threshold difference between the reactions containing target gene primer pair and the 18S rRNA housekeeping gene primer pair in each sample. Each experiment was repeated at least two times in triplicates. Data were expressed as means+/−S.D. of the relative gene expression levels. The primers were designed using the Primer3 web utility to obtain the following sequences (all murine): 18S (forward) 5'-CCCTGCCCTTTGTACACACC-3' (SEQ ID NO: 8); 18S (reverse) 5'-CGATCCGAGGGCCTCACTA-3' (SEQ ID NO: 9); Runx2 (forward) 5'-CCGCACGACAACCGACCAT-3' (SEQ ID NO: 10); Runx2 (reverse) 5'-AGCCACCAAG-GCTGGAGTCTT-3' (SEQ ID NO: 11).

5.8 Bone Mineralization Assays

Calcium deposition in osteogenically differentiated C2C12 cells was evaluated using an Alizarin Red S (ARS) staining method. The transfected and untransfected cells were cultured in 100 ng mL$^{-1}$ BMP-2 supplemented media in 24 well plates for two weeks. Media were changed every 48 hours. On day 14, cells were fixed with 4% paraformaldehyde, then stained with a 2% solution of ARS dye at pH 4.2. After 20 minutes incubation followed by washing, the samples were analyzed under a bright field microscope.

5.9 Statistical Analysis

Each experiment was repeated two to three times independently. Measurements in each experiment were made in triplicate. All results are expressed as mean+/−standard deviation (S.D.). The statistical significance was analyzed by Student's t test or ANOVA. A p value <0.05 was considered to be statistically significant.

5.10 Cytotoxicity

The use of polymer and liposome based carriers is often limited by their inherent cytotoxicities. The cytotoxicity caused by the DOTAP/siRNA/anionic polyelectrolyte nanocomplexes was determined by monitoring the metabolic activity of C2C12 cells transfected with the nanocomplexes 24 hours post transfection. When mixed at a 10:1 weight ratio to give a net charge ratio 3.8, the DOTAP/siRNA lipoplexes reduced the metabolic activity of the C2C12 cells to 86% of the untreated cells. The ternary complexes of the DOTAP/siRNA with PPAA or PPAA-g-JEFFAMINE® provided a cytoprotective effect, with 95% basal metabolic activity observed at an overall charge ratio of 1.0 irrespective of the copolymer graft density. When the DOTAP:siRNA ratio was increased to 20:1 to give the initial lipoplex charge ratio (+/−) of 7.6, the metabolic activity was further reduced in all samples but again the anionic polyelectrolytes provided a cytoprotective effect Nonetheless, an initial DOTAP/siRNA charge ratio of 3.8 was used for subsequent studies.

5.11 Results.

The efficient delivery of siRNA cargo, and consequently the silencing of the targeted gene, is the cumulative outcome of several steps, including survival of the complexes in physiological environment, efficient internalization of the complexes by the cells, and their escape from the endosomolytic pathway. Construction of a delivery system that is effective in each of these ways remains a formidable challenge to the field. The polyelectrolyte PPAA (ungrafted) demonstrates outstanding membrane disruption ability at endosomal pH and forms nanocomplexes with DOTAP/siRNA of reasonable size and charge, but the transfection carried out by DOTAP/siRNA/PPAA resulted in inefficient silencing of the target gene. Accumulation of serum proteins on the surface of nanocomplexes may disrupt their interaction with the plasma membrane and thereby affect nucleic acid delivery.

To address this limitation, we developed copolymers of PPAA grafted with JEFFAMINE® M2070, a copolymer of ethylene oxide and propylene oxide with a terminal amine. Grafting of the JEFFAMINE® onto PPAA abates the low pH membrane disruption activity of the copolymer but augments significantly the resistance to serum attack. 10c,d Furthermore, grafting of JEFFAMINE® chains onto the PPAA imparts non-ionic amphiphilic character to the polyelectrolyte, enhancing its tendency to interact with lipophilic cell membranes. Among the graft copolymers that we have synthesized to date, PPAA-g-1% JEFFAMINE® exhibits the greatest extent of membrane interaction. Our results with antisense oligonucleotides have suggested that a minimum level of grafting is necessary for serum stability, but once this is attained, a lower hydrophilic-lipophilic balance is desirable, as is the case for the graft copolymers with low extent of grafting and incorporation of the more lipophilic propylene oxide moieties (i.e., JEFFAMINE®). In this light, it is reasonable that the nanocomplexes formed in the presence of PPAA-g-1% JEFFAMINE® exhibit maximum efficiency to knock down Runx2 expression and inhibit the early and late phenotypic markers of osteoblastic differentiation in C2C12 cells. Transfection of C2C12 cells by specific siRNA for 4 hours efficiently knocked down expression of Runx2 in myoprogenitor cells by 24 hours post transfection. Notably, the biological effect of single-dose silencing was maintained at a phenotypic level 2 weeks post transfection.

Further, by conjugating bone targeting ligand alendronate to the PAO moiety of the graft co-polymer to achieve active targeting of bone tissue we have developed an effective polymer/lipid-based nanoparticle delivery system for siRNA that has targeted affinity for bone tissue. The bone binding ligand ALN was successfully incorporated as a c-graft on the PPAA backbone via short PEG spacer chains. The cytotoxicity assay indicated that PPAA-g-PEG and PPAA-g-PEG-ALN had excellent cell-compatibility. The HA binding assay confirmed that the strong affinity of ALN towards HA allowed the quick binding of nanocomplexes with HA. Confocal laser scanning microscopy proved the efficient cell uptake of Cy5-labeled siRNA-loaded nanocomplexes. In vitro transfection of myoprogenitor cells C2C12, consequent silencing of transcription factor Runx2 revealed that DOTAP/siRNA/PPAA-g-PEG or DOTAP/siRNA/PPAA-g-PEG-ALN nanocomplexes were equally capable of efficiently eliciting RNA intereference. However, DOTAP/siRNA/PPAA-g-PEG-ALN exhibited preferential targeting of bone mineral in the oseogenically differentiated C2C12 culture as compared to that observed in the case of DOTAP/siRNA/PPAA-g-PEG nanocomplexes.

Thus, it has now been demonstrated that silencing of Runx2, mediated by potent delivery using the serum-stable DOTAP/siRNA/PPAA-g-1% JEFFAMINE® formulation, is sufficient to halt the osteogenic switch driven by BMP-2. The fact that silencing was substantial and robust in serum-containing media bodes well for use of this delivery formulation in vivo.

Example 6

In Vitro and In Vivo Delivery of Antisense Oligonucleotides Using Poly(Alkylene Oxide)-Poly(Propylacrylic Acid) Graft Copolymers in Conjunction with Cationic Liposomes 6.1. Synthesis of Poly(Alkylene Oxide) (PAO) Graft Copolymers Poly(propylacrylic acid) (50 mg, 0.44 mol of repeat units) was taken in a dry 10 mL round bottomed flask. HOBt (9 mg, 0.044 mmol) and diisopropylcarbodiimide, DIPC (10.2 µL, 0.044 mmol) were added to the flask. Dry THF (5 mL) was added to the flask and the reaction was stirred at room temperature for 45 min After this, amine-terminated JEFFAMINE® or PEO (0.0044, 0.022, 0.044 moles corresponding to 1, 5, 10 mol % target graft densities, respectively) was added and the reaction was stirred at 50° C. for 30 hrs. After the reaction time, THF was removed and dried product was resuspended in a solution of 10% by volume 1N NaOH and 90% by volume PBS, pH 7.4. This mixture was transferred to a Pierce Dialyzer cassette (MWCO 10000 Da) and dialyzed against distilled water for 3 days, with three buffer changes in the first 6 hrs, followed by one buffer change every 12 hrs for the remaining time period. The product was then removed, lyophilized and characterized by proton NMR using DMSO as the solvent.

6.2. Characterization of PAO Graft Copolymers

Using the amide peak for NMR integration is the most direct and accurate method to determine the degree of conjugation, however since the peak is very small for integration, this method is inaccurate when using small quantities of material for analysis. Hence, the following methods have been used: 1) For the graft copolymers with JEFFAMINE®M2070: the peaks of CH3 on PPAA and CH3 on JEFFAMINE® are used. 100% grafting is indicated by a 1:10 ratio of CH3 on PPAA and CH3 on propylene oxide of JEFFAMINE®, respectively, 2) For the graft copolymers with JEFFAMINE® M2005, the peaks of CH3 on PPAA and CH3 on JEFFAMINE® are used. 100% grafting is indicated by a 1:29 ratio of CH3 on PPAA and CH3 on propylene oxide of JEFFAMINE®, respectively, 3) For the graft copolymers with PEO, the peaks of H on CH3 of PPAA and H on EO of PEO are used. 100% grafting is indicated by a 3:180 ratio of H on CH3 of PPAA and H on CH3 of EO, respectively. For PPAA-g-1 mol % JEFFAMINE® M2070: $^1$H NMR (DMSO-d6) δ 0.8 (s, CH3), 1 (C—CH3), 3.5 (CH2, JEFFAMINE®) are 3, 0.98, 2.8, respectively. For PPAA-g-5 mol % JEFFAMINE® M2070: $^1$H NMR (DMSO-d6) δ 0.8 (s, CH3), 1 (C—CH3), 3.5 (CH2, JEFFAMINE®) are 3, 2.38, 8.31, respectively. For PPAA-g-10 mol % JEFFAMINE® M2070: $^1$H NMR (DMSO-d6) δ 0.8 (s, CH3), 1 (C—CH3), 3.5 (CH2, JEFFAMINE®) are 3, 3.3, 14.23, respectively. For PPAA-g-1 mol % JEFFAMINE® M2005: $^1$H NMR (DMSO-d6) δ 0.8 (s, CH3), 1 (C—CH3), 3.5 (CH2, JEFFAMINE®) are 3, 1.87, 2.01, respectively. For PPAA-g-1 mol % PEO: $^1$H NMR (DMSO-d6) δ 0.8 (s, CH3), 3.3-3.5 (—CH2CH2O—) are 3, 2.63, 3.91, respectively. For PPAA-g-5 mol % PEO: $^1$H NMR (DMSO-d6) δ 0.8 (s, CH3), 3.3-3.5 (—CH2CH2O—) are 3, 6.31, 16.23, respectively. For PPAA-g-10 mol % PEO: $^1$H NMR (DMSO-d6) δ 0.8 (s, CH3), 3.3-3.5 (—CH2CH2O—) are 3, 10.32, 31.71, respectively.

6.3. Hemolysis Assay

The ability of PPAA and the grafted polymers to disrupt membranes was assessed using a hemolysis assay. Briefly, solutions of PPAA and graft copolymers at equivalent moles of carboxylic acid groups were formulated in buffers at pH values ranging from 5.0 to 7.0. Freshly washed red blood cells (RBCs) were added at a concentration of 108 cells/mL, incubated in a water bath at 37° C. for 1 hr, and then centrifuged for 4 min at 400 g to pellet the intact cells. The absorbance of the supernatant, consisting of RBC lysate, was measured at 540 nm using a UV spectrophotometer (Thermo Spectronic) and normalized to conditions consisting of RBCs in equivalent buffers in the absence of polymer (negative control) and RBCs in distilled water (positive control). RBCs were used within two days of isolation.

6.4. Calcein Dye Leakage from Dye-Loaded DPPC Liposomes

DPPC liposomes were prepared following the general protocol provided by Avanti Polar Lipids. Briefly, the first step involved obtaining a thin lipid film, followed by hydration of the lipid film with calcein dye by agitation and heating/stirring at 50° C. for 2 hrs (Note: this temperature is greater than the phase temperature of the lipid). The weight ratio of DPPC lipid to calcein was 1:3 to ensure full loading of dye with excess. Further, the samples were agitated and sonicated for 15 minutes to form lamellar vesicles, followed by 5 cycles of freeze/thaw and extrusion using a 100 nm polycarbonate membrane. Finally, unloaded calcein dye was separated from DPPC liposomes using a Sephadex column. For the membrane penetration assay, varying amounts of PPAA and graft copolymers were mixed with 0.68 mM calcein loaded in DPPC liposomes and allowed to incubate for 1 hr at 37° C. in a pH 7.4 buffer solution. Subsequently, fluorescence resulting from release of calcein dye was measured at an excitation wavelength of 490 nm and emission of 520 nm and normalized to a positive control consisting of dye-loaded DPPC liposomes incubated with Triton X-100 and a negative control consisting of dye-loaded DPPC without added polymer or surfactant.

6.5. Cell Culture Evaluation

A2780 human ovarian cancer cells were obtained from American Type Culture Collection. Cells were maintained in RPMI 1640 medium supplemented with 10% FBS, 100 U/mL penicillin, and 100 ng/mL streptomycin. Nanocomplexes were prepared utilizing a two-step procedure in which AON and DOTAP are initially incubated to form binary complexes, and subsequently anionic polyelectrolyte is added. All of the complexes were prepared using a DOTAP/AON charge ratio (+/−) of 4.7 and a DOTAP/AON/Polymer net charge ratio of 1.0, where the net charge ratio is defined as the ratio of the moles of DOTAP amine groups to the sum of the moles of AON phosphate groups and PPAA carboxylic acid groups, with the latter assumed to be 33% ionized at pH 7.4.

6.6. In Vitro Cell Metabolic Activity

Cells were cultured on 96-well plates and treated with the various graft copolymer formulations at 2 ng/mL AON concentration. Cell metabolic activity was determined using the MTS assay at various time points (48, 72 and 96 hrs post-treatment) using the CellTiter 96® AQueous Non-radioactive Cell Proliferation (MTS) kit (Promega, Madison, Wis., U.S.A).

6.7. In Vitro Gene Silencing

A2780 cells were seeded onto 12-well plates at 105 cells/mL (with 1 mL volume per well) ~18 hr prior to AON treatment. The bcl-2 AON sequence (5'-TCTCCCAGCGT-GCGCCAT-3' (SEQ ID NO: 12)) was used at a concentration of 300 nM. Complexes were prepared in a volume of 200 mL, followed by mixing with 10% FBS-containing medium and addition to each well. For control samples, complexes were substituted with 200 µL of PBS. After 4 hours of exposure, medium containing complexes was aspirated and replaced with fresh medium. Cells were assayed for bcl-2 gene expression 24 hrs post-AON treatment using real-time PCR, with 18S as the internal standard. The $\Delta\Delta Ct$ method was used to calculate % bcl-2 gene expression.

6.8 In Vivo Evaluation; Animal Tumor Model

All animal experiments were carried out in accordance with the protocol approved by the Institutional Animal Care and Use Committee. An animal model of human ovarian carcinoma xenografts was created. Briefly, A2780 human ovarian cancer cells were passaged at 70% cell density, during their peak growth phase. At this point, $5-8\times10^6$ cells were transplanted subcutaneously into the flanks of athymic nude mice (6-8 weeks old, —20 g weight). The tumor size was measured with a caliper and its estimated volume was calculated as d2×D/2 where d and D are the minor and major axes of the roughly elliptically-shaped tumor surface, respectively.

6.9. Biodistribution

When the tumor reached a size of about 400 mm3 (15-25 days after transplantation), 250 µL of the various formulations containing 0.625 mg Cy5.5-AON/kg were administered to the mice by intraperitoneal (i.p.) injection. After 24 hr, mice were sacrificed, and their tissues were collected and imaged by the IVIS Imaging System (Xenogen, Alameda, Calif.). All fluorescence values were adjusted by subtracting autofluorescence signal from tissues collected from mice treated with PBS. Organs (liver, kidney, heart, spleen, lung and tumor) were excised and weighed for normalization.

6.10. Bcl-2 Intratumoral Gene Silencing

Silencing of the bcl-2 gene in tumors was measured 24 hr after mice were treated by intratumoral injection of 250 µL of the various formulations containing 0.625 mg of the antisense AON/kg. Following treatment, each tumor was excised and homogenized. The mRNA from cells was extracted using RNeasy Mini Kit (Qiagen, Valencia, Calif.), and cDNA was synthesized using Ambion RETROscript® Kit (Invitrogen, Carlsbad, Calif.). Using the cDNA, the rt-PCR reaction was conducted to amplify 18S and bcl-2 and detected using QuantiTect SYBR Green PCR kit (Qiagen, Valencia, Calif.). Bcl-2 gene expression in treated mice was normalized to that of untreated animals.

6.11. Statistical Analysis

All statistical analyses were performed by a one-way ANOVA test with Tukey post-hoc pairwise comparison test. Data was considered statistically significant when p value was less than 0.05. All analyses were performed using Kaleidagraph v4.

6.12. Bcl-2 Gene Silencing in Cell Culture

The ability of graft copolymer complexes to deliver AON in serum-containing media and to silence target bcl-2 gene was evaluated using the A2780 human ovarian carcinoma cell line. The expression of bcl-2 gene was evaluated 24 hrs post-treatment, which provides sufficient time for cellular internalization of AON and turnover of existing mRNA. The binary complex of DOTAP/AON induced only modest gene silencing, with 80% bcl-2 gene expression relative to that of untreated cells. The addition of PPAA to DOTAP/AON complexes improved the antisense gene silencing effect, reducing the bcl-2 expression to 40% of the untreated control. This enhanced silencing effect caused by the addition of PPAA had also been observed using a CHO-d1EGFP cell line. The ternary nanoparticle complexes with the lowest graft density copolymers (1% JEFFAMINE® M 2070 and 1% PEO) further improved antisense gene silencing, reducing bcl-2 gene expression levels to 10 and 15%, respectively. However, the 5 and 10% graft density JEFFAMINE® and PEO copolymers progressively decreased gene silencing, with bcl-2 gene expression levels similar to control, untreated cells. Some non-specific silencing was observed when an irrelevant sequence was used, as is common with standard AONs. The extent of non-specific gene silencing also decreased with increasing graft density, suggesting a role for carrier-cell interactions in the non-specific silencing. For the most effective treatments using 1% PAO graft copolymers, the silencing effects with bcl-2 sequence were significant compared to treatments with scrambled AON sequence.

6.13. Biodistribution

As a first evaluation of the disposition of these graft copolymer nanocomplexes in vivo, the biodistribution of Cy5.5-AON delivered using DOTAP/AON ('no polymer') and 1%, and 10% PAO-graft copolymer delivery systems was determined in mice with xenograft tumors formed with the same A2780 human ovarian cancer cells used for the in vitro studies. These conditions were chosen to determine the effects of polymer chemistry, PEO vs. JEFFAMINE®, and grafting density, low (1 mol %) vs. high (10 mol %). At AON concentrations of 2 ng/mL or lower (that used for physical and in vitro studies), all formulations formed stable complexes with DOTAP/AON with negligible free AON in solution. For in vivo studies, an AON concentration of 50 ng/mL was determined to be the minimum concentration necessary for the detection of Cy5.5 AON using IVIS imaging system. At this concentration of DOTAP/AON nanoparticles, the addition of PPAA destabilized the complex as seen by precipitation of Cy5.5.-AON in solution and values greater than 50% free (i.e. unbound AON) in fluourescence quenching studies (data not shown). On the other hand, addition of PPAA-g-PAO stabilized the complex, with minimum free AON in solution, even at high concentrations (data not shown). On this basis, treatments with PPAA were eliminated from in vivo studies since sufficient nanoparticle concentrations could not be achieved.

For all conditions, the accumulation of AON 24 hours following i.p. injection was greatest in the kidney, compared to the spleen, liver, lung and tumor. This likely represents Cy5.5-AON released from nanocomplexes throughout the body and subsequently cleared to the kidney by renal filtration, as opposed to direct distribution of the nanocomplexes to the kidney. A greater percentage of Cy5.5-AON was found in all organs at 24 hours when delivered as part of 1% PAO nanocomplexes, suggesting that these particles persisted longer in circulation compared to DOTAP/AON, with which the AON was presumably cleared at earlier time points.

The treatments with 1 mol % JEFFAMINE® M2070 ('Pg1% J70') and 1 mol % PEO ('Pg1% PEO') showed highest distribution to A2780 xenograft tumors compared to DOTAP/AON ('No polymer') and 10% PAO grafts. Although it is known that the accumulation of AON in the tumor is low for untargeted particles compared to targeted particles, the serum-stable nanoparticles with 1% PAO grafts display a significant degree of accumulation in the tumor compared to other formulations tested in this study.

6.14. Bcl-2 Gene Silencing in Tumors

From the biodistribution data, it was determined that the 1% PAO graft copolymer delivery systems were most effective in delivering AON to the tumors, compared to control (DOTAP/AON) and 10 mol % PAO graft copolymer systems. To determine whether AON delivered to tumors with these formulations can reach cells in active form, the ability to induce antisense gene silencing in A2780 xenograft tumors was evaluated for the most promising PAO delivery systems. Treatments with the ternary nanoparticle complexes of PPAA-g-1% JEFFAMINE® M 2070 and PPAA-g-1% PEO reduced expression of the bcl-2 gene to 40 and 60%, respectively, at 24 hrs post-treatment, while the binary DOTAP/AON complex and all of the delivery systems with scrambled AON did not reduce gene expression. The degree of gene silencing was significant compared to treatments with scrambled sequence (~100% expression of bcl-2 gene), which demonstrated the sequence-specific nature of the antisense gene silencing effect.

These studies show a definite positive relationship between lipophilicity (or inversely between HLB) of PPAA-g-PAO graft copolymers and membrane association. This relationship appears to be critical to the finding that lower HLB values for these copolymers lead to greater gene silencing in serum containing media when used in conjunction with otherwise ineffective DOTAP/AON, with the proviso that ungrafted PPAA is ineffective in serum, presumably due to serum-mediated aggregation or degradation. Notably, we have found that the 1 mol % JEFFAMINE® and PEO graft copolymer delivery systems proved to be most effective for antisense delivery not only in cell culture but also in vivo. Specifically, these polymers have shown particle stability, increased tumor accumulation upon systemic administration and bcl-2 target gene silencing upon intra-tumoral administration. As such, the DOTAP/PPAA-g-PAO system shows considerable promise for delivery of AONs for gene silencing in vivo.

Although the invention herein has been described with reference to particular embodiments, it is to be understood that these embodiments are merely illustrative of the principles and applications of the present invention. It is therefore to be understood that numerous modifications can be made to the illustrative embodiments and that other arrangements can be devised without departing from the spirit and scope of the present invention which is defined by the following claims.

All references cited herein are incorporated by reference in their entirety.

What is claimed is:

1. A graft copolymer polyelectrolyte complex comprising:
   (1) an anionic graft copolymer comprising:
      (i) a backbone comprising a poly(alkylacrylic acid); and
      (ii) one or more polyetheramine pendent chains covalently attached to said copolymer backbone as amides of acrylic acid groups, wherein said pendent chains predominantly comprise ethylene oxide repeating units;
   wherein said copolymer has a graft density between about 0.1 and about 25 mole percent;
   (2) one or more anionic, cationic or polyelectrolyte therapeutic agents; and
   (3) optionally, a liposome which optionally comprises a further therapeutic agent;
   wherein when said anionic, cationic or polyelectrolyte therapeutic agent is a polynucleotide molecule, said liposome, optionally comprising said further therapeutic agent, is also present; and wherein said pendent chains further comprise one or more ligands that target a microbial biofilm or a planktonic microbe; or said pendent chains further comprise one or more ligands which comprise a phosphonate molecule that targets bone tissue.

2. The complex of claim 1, wherein the copolymer backbone comprises poly(propyl acrylic acid) or poly(methacrylic acid).

3. The complex of claim 1, wherein said copolymer has a graft density between about 0.5 and about 5 mole percent.

4. The complex of claim 1, wherein said liposome is present.

5. The complex of claim 1, wherein said anionic, cationic or polyelectrolyte therapeutic agent is stabilized toward biological degradation in vivo.

6. A functional nanoparticle comprising the complex of claim 1, wherein said nanoparticle provides in vivo delivery of the anionic, cationic or polyelectrolyte therapeutic agent.

7. A method of treating a patient in need thereof with a polyelectrolyte therapeutic agent comprising the steps of:

(1) formulating the complex of claim 1 with one or more pharmaceutically acceptable carriers to provide a pharmaceutical composition; and
(2) administering said pharmaceutical composition to said patient in an amount effective to treat said patient.

8. The method of claim 7, wherein said anionic, cationic or polyelectrolyte therapeutic agent is selected from the group consisting of antibacterial agents, anticancer agents, wound treatment agents and tissue regeneration agents.

9. The method of claim 7, wherein the administration is via oral, enteral, parenteral or topical delivery.

10. The method of claim 7, wherein said pharmaceutical composition is selected from the group consisting of injectable aqueous solutions, injectable aqueous dispersions, emulsions, gels, pastes, aerosols, sprays, coatings, hydrogels, topical creams, topical ointments, natural and synthetic polymeric fibers, porous ceramics, polymeric and ceramic composites, and wound treatment compositions.

11. A method of preparing a graft copolymer-polyelectrolyte complex of claim 1, comprising the steps of:
   (1) providing an aqueous mixture of an anionic graft copolymer comprising:
      (i) a backbone comprising a poly(alkyl acrylic acid); and
      (ii) one or more polyetheramine pendent chains covalently attached to said copolymer backbone as amides of acrylic acid groups, wherein said pendent chains predominantly comprise ethylene oxide repeating units;
   wherein said copolymer has a graft density between about 0.1 and about 25 mole percent;
   (2) adding one or more polyelectrolytes to form a polyelectrolyte-copolymer mixture;
   (3) optionally adding an aqueous mixture containing a liposome which optionally comprises a further therapeutic agent, to form a liposome-containing polyelectrolyte-copolymer mixture; and
   (4) allowing said polyelectrolyte-copolymer mixture or said liposome-containing polyelectrolyte-copolymer mixture to self-assemble in the aqueous medium to form said complex, which further forms nanoparticles.

12. A graft copolymer polyelectrolyte complex comprising:
(1) an anionic graft copolymer comprising:
  (i) a backbone comprising a poly(alkylacrylic acid); and
  (ii) one or more polyetheramine pendent chains covalently attached to said copolymer backbone as amides of acrylic acid groups, wherein said pendent chains predominantly comprise ethylene oxide repeating units;
wherein said copolymer has a graft density between about 0.1 and about 25 mole percent;
(2) one or more anionic, cationic or polyelectrolyte therapeutic agents; and
(3) optionally, a liposome which optionally comprises a further therapeutic agent;
wherein said anionic, cationic or polyelectrolyte therapeutic agent is selected from the group consisting of vancomycin, telavancin, daptomicin, mepivacaine, lidocaine, bupivacaine, benzocaine and procaine.

13. The complex of claim 12, wherein said anionic, cationic or polyelectrolyte therapeutic agent is daptomicin.

14. The complex of claim 12, wherein said anionic, cationic or polyelectrolyte therapeutic agent is selected from the group consisting of mepivacaine, lidocaine, bupivacaine, benzocaine and procaine.

* * * * *